(12) United States Patent
Ogata

(10) Patent No.: US 6,714,296 B2
(45) Date of Patent: Mar. 30, 2004

(54) METHOD AND APPARATUS FOR INSPECTING PHOTOSENSITIVE MATERIAL FOR SURFACE DEFECTS

(75) Inventor: Kenichi Ogata, Fujinomiya (JP)

(73) Assignee: Fuji Photo Film. Co., Ltd., Kanagawa (JP)

(*) Notice: Subject to any disclaimer, the term of this patent is extended or adjusted under 35 U.S.C. 154(b) by 0 days.

(21) Appl. No.: 10/274,044

(22) Filed: Oct. 21, 2002

(65) Prior Publication Data

US 2003/0090653 A1 May 15, 2003

(30) Foreign Application Priority Data

Oct. 25, 2001 (JP) ......................... 2001-328072

(51) Int. Cl.[7] ............................... G01N 21/00
(52) U.S. Cl. ................................... 356/237.2
(58) Field of Search ................ 356/237.1–237.3; 250/559.4, 559.41, 559.42

(56) References Cited

U.S. PATENT DOCUMENTS 6,088,092 A * 7/2000 Chen et al. ............... 356/237.2

2002/0149771 A1 * 10/2002 Yamaguchi et al. ........ 356/431

FOREIGN PATENT DOCUMENTS

JP 53-118089 10/1978

* cited by examiner

Primary Examiner—Michael P. Stafira
(74) Attorney, Agent, or Firm—Young & Thompson

(57) ABSTRACT

The surface defect inspection method and apparatus are capable of inspecting a photosensitive material for defective surface portions with efficiency by using a reflex-type optical sensor. The surface defect inspection apparatus has a reflex-type optical sensor. A thermal-developable photosensitive material is irradiated with inspection light from a light source. Reflected light from the photosensitive material is received by a light-receiving portion of the optical sensor and a defective surface portion is detected from the reflected light. A mask is attached to the light-receiving portion to cut out specular reflected light, thereby enabling a change in the quantity of diffuse reflected light to be directly detected. Therefore, even a defective surface portion where only a small diffuse reflectance is recognized can be detected with efficiency.

9 Claims, 5 Drawing Sheets

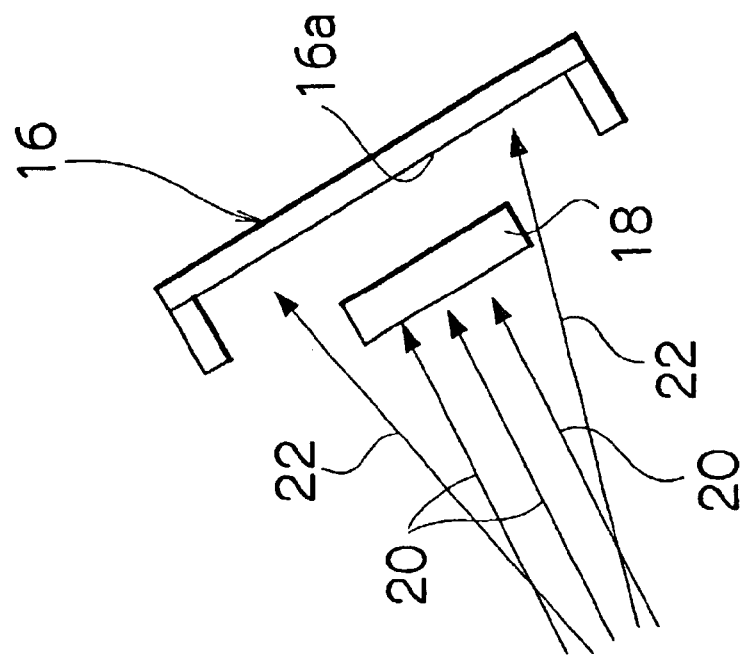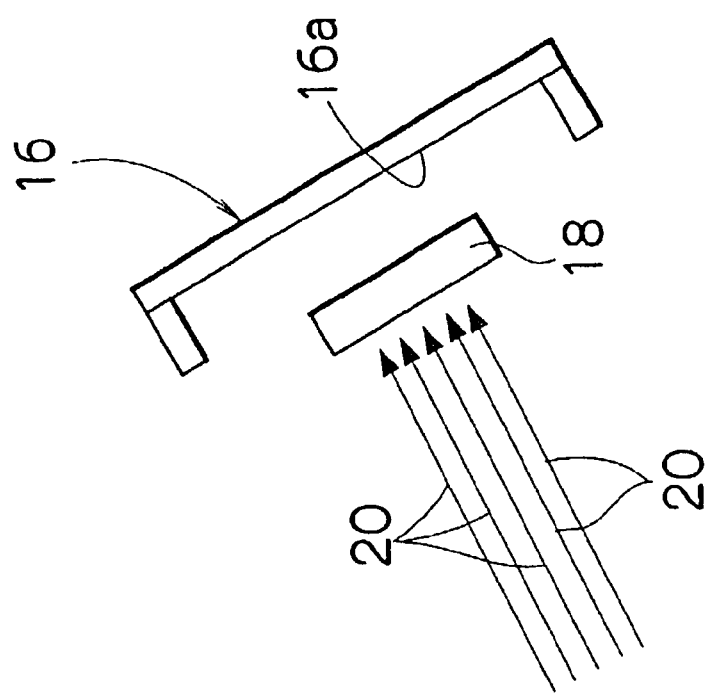

DEFECTIVE PORTION

NORMAL PORTION

METHOD AND APPARATUS FOR INSPECTING PHOTOSENSITIVE MATERIAL FOR SURFACE DEFECTS

BACKGROUND OF THE INVENTION

1. Field of the Invention

The present invention relates to a method and apparatus for inspecting a photosensitive material for surface defects and, more particularly, to a method and apparatus for inspecting a thermal-developable photosensitive material for defective surface portions by using a reflex-type optical sensor.

2. Description of the Related Art

In recent years, in the field of production of films for medical diagnosis and photoengraving films, there has been a strong demand for reductions in the amounts of waste processing solutions from the viewpoint of environmental protection and space saving. Therefore, techniques are required which relate to a thermal-developable photosensitive material formed as a film for medical diagnosis and a photoengraving film and capable of efficient exposure with a laser image setter or a laser imager and forming a black image having a high resolution and a high degree of sharpness. The thermal-developable photosensitive material has the advantages of requiring no processing chemical solution and enabling clients to be supplied with a thermal-development processing system which is simpler and is designed to avoid any damage to an environment.

The thermal-developable photosensitive material is made by applying materials for a photosensitive layer, a protective layer, etc., to a flexible substrate (hereinafter referred to as a web). In the thermal-developable photosensitive material made in this manner, there is a possibility of a break, a contamination, a pinhole, a streak defect or the like existing in the surface on the photosensitive layer side. Therefore, it is necessary to detect such defective surface portions of the thermal-developable photosensitive material.

As a method of optically inspecting a photosensitive material for defective surface portions, a reflection-type method is known in which a photosensitive material is inspected by irradiating the surface of the photosensitive layer with inspection light from a laser oscillator and by using light reflected by the surface of the photosensitive layer. Another method known as a method of optically inspecting a photosensitive material is a transmission-type method in which a photosensitive material is inspected by monitoring light transmitted through the photosensitive layer. It is advantageous to use the transmission-type method rather than the reflection-type method for detection of a pinhole or a coating discontinuity in a photosensitive layer, which is a fatal defect.

The above-described thermal-developable photosensitive material used without a step for dissolution in a solution unlike conventional photosensitive materials which undergo solution-development has a high degree of transparency and only a small difference in density at a defective portion in its surface. Therefore, it is difficult to detect defective surface portions of the thermal-developable photosensitive material by using a transmission-type optical sensor.

Japanese Patent Application Publication No. 53-118089 discloses a method of detecting defective surface portions with a reflex-type sensor. That is, a defective surface portion of the thermal-developable photosensitive material has a diffuse reflectance higher than that of the normal portion and the quantity of specular reflected light from the defective portion is smaller than the quantity of the specular reflected light from the normal portion. As shown in FIG. 6(A), when the normal portion is irradiated with inspection light, a large amount of the specular reflected light 2 is received by a light-receiving portion 1. In contrast, when the defective surface portion is irradiated with inspection light, the quantity of the specular reflected light 2 is reduced, as shown in FIG. 6(B). It is possible to detect the defective surface portion in accordance with this reduction in quantity of light from the normal value.

However, there is a problem that the reflex-type optical sensor is incapable of detecting a defective portion with accuracy when the change in diffuse reflectance across the defective surface portion is small. That is, when the change in diffuse reflectance across a defective surface portion is small, the change in the quantity of the specular reflected light 2 is also small. Under this condition, the resulting change in the quantity of light received by the light-receiving portion 1 is extremely small since part of diffuse reflected light 3 is received by the light-receiving portion 1. For this reason, defective surface portions across which only a small change in diffuse reflectance is recognized cannot be detected with accuracy by using the reflex-type optical sensor. The light-receiving area of the light-receiving portion 1 may be reduced to avoid receiving of diffuse reflected light 3. The sensitivity is thereby improved to some degree. However, if the light-receiving area is reduced, the adaptability of the optical sensor to inspection of other objects which may be selected is reduced. This problem is encountered not only in the case of detection of defects in the thermal-developable photosensitive material but also in the case where defect portions in a transparent photosensitive material are detected with a reflex-type optical sensor.

SUMMARY OF THE INVENTION

In view of the above-described circumstances the present invention is achieved and, an object of the present invention is to provide a surface defect inspection method and apparatus capable of inspecting a photosensitive material for defective surface portions with efficiency by using a reflex-type optical sensor.

To attain the above-described object, the present invention is directed to a surface defect inspection method of inspecting a photosensitive material for defective surface portions by using a reflex-type optical sensor, comprising the steps of: irradiating the photosensitive material with inspection light from a light-emitting portion of the reflex-type optical sensor; receiving, through a light-receiving portion of the reflex-type optical sensor, light in a reflected part of the inspection light reflected by the photosensitive material while cutting out specular reflected light in the reflected part of the inspection light; and checking a defective surface portion in the photosensitive material in accordance with a change in a quantity of the light received through the light-receiving portion.

The present invention is also directed to a surface defect inspection apparatus which inspects a photosensitive material for defective surface portions by using a reflex-type optical sensor, wherein the reflex-type optical sensor comprises: a light-emitting portion which irradiates the photosensitive material with inspection light; a light-receiving portion which receives light in a reflected part of the inspection light reflected by the photosensitive material; and a shielding member which cuts out specular reflected light in the reflected part of the inspection light traveling to the light-receiving portion.

According to the present invention, specular reflected light in the reflected part of inspection light reflected by the photosensitive material is cut out and only diffuse reflected light in the reflected part of the inspection light is received, thereby increasing changes in the quantity of received light due to defective surface portions and enabling the defective surface portions to be checked with accuracy.

Preferably, a transmission-type optical sensor is used as well as the reflex-type optical sensor to enable a pinhole, a coating discontinuity or the like, which are detected more preferably by the transmission type, to be checked with efficiency.

Preferably, a selection can be made from a state where the specular reflected light is cut out and a state where the specular reflected light is not cut out, thereby enabling other photosensitive materials requiring receiving specular reflected light to be inspected for defective surface portions with efficiency.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIGS. 2(A) and 2(B) are schematic side views of a structure of a light-receiving portion of a reflex-type optical sensor;

DETAILED DESCRIPTION OF THE PREFERRED EMBODIMENTS

Preferred embodiments of a method and apparatus for inspecting surface defects in a photosensitive material in accordance with the present invention will be described in detail with reference to the accompanying drawings.

A principle of the surface defect inspection method and apparatus in accordance with the present invention will be described with respect to a thermal-developable photosensitive material by way of example.

Figure 1:
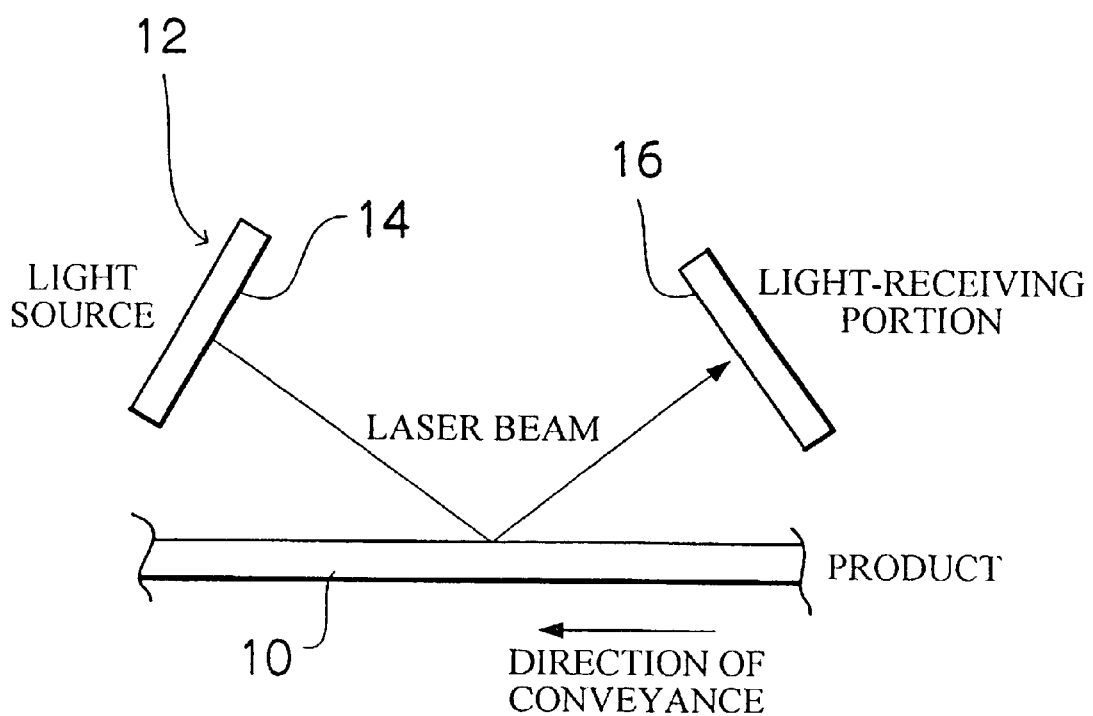
FIG. 1 is a side view of an arrangement for explaining a principle of a defect inspection method and apparatus in accordance with the present invention.

A thermal-developable photosensitive material is made by applying materials for a photosensitive layer, a protective layer, etc., to a flexible substrate. There is a possibility of this product having a defective surface portion such as a pinhole or a streak defect in its surface. In the present embodiment, therefore, the surface of a thermal-developable photosensitive material web 10 is inspected with a reflex-type optical sensor 12 while the photosensitive material 10 is being conveyed in the direction of the arrow as shown in FIG. 1.

The reflex-type optical sensor 12 has a light source (light-emitting portion) 14 and a light-receiving portion 16. The thermal-developable photosensitive material 10 is irradiated with inspection light (laser light) from the light source 14, and reflected light from the thermal-developable photosensitive material 10 is received by the light-receiving portion 16. A defective surface portion is detected in accordance with a change in the quantity of light received by the light-receiving portion 16.

As shown in FIGS. 2(A) and 2(B), a mask (shielding member) 18 is detachably mounted so as to face a light-receiving surface 16a of the light-receiving portion 16. The mask 18 cuts out specular reflected light 20 in the reflected light received by the light-receiving portion 16. Therefore, if the reflected light consists of only the specular reflected light 20, substantially no light is received by the light-receiving portion 16, as shown in FIG. 2(A). In the case where the specular reflected light 20 and diffuse reflected light 22 exist as shown in FIG. 2(B), only the diffuse reflected light 22 is received.

A defective surface portion of the thermal-developable photosensitive material 10 has a diffuse reflectance higher than that of the normal portion. When the defective surface portion is irradiated with inspection light, the light-receiving portion 16 receives only the diffuse reflected light 22, as shown in FIG. 2(B). On the other hand, when the normal portion is irradiated with inspection light, the quantity of light received by the light-receiving portion 16 is approximately zero since substantially no diffuse reflected light 22 exists as shown in FIG. 2(A). Thus, if a defective surface portion exists, the diffuse reflected light 22 is markedly increased due to the defective surface portion to increase the quantity of light received by the light-receiving portion 16. Consequently, the defective surface portion can be detected with accuracy.

Figure 6:
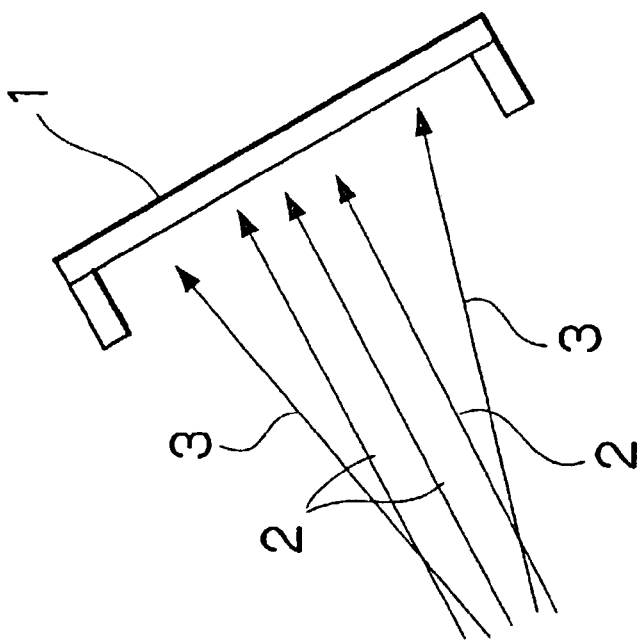
FIGS. 6(A) and 6(B) are schematic side views of a light-receiving portion of a conventional reflex-type optical sensor.
Figure 6:
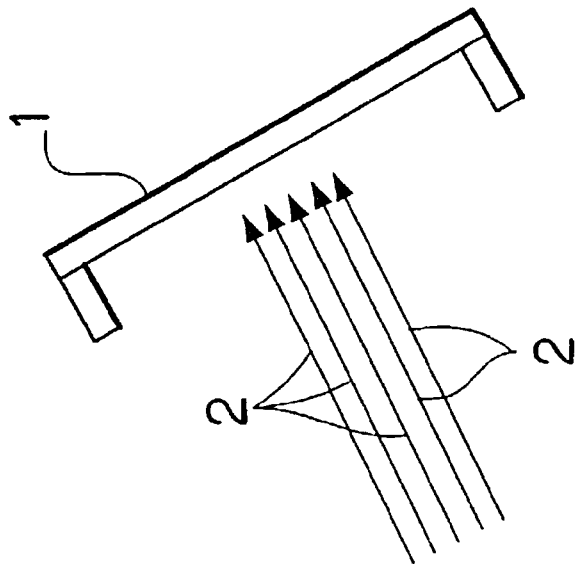

The mask 18 attached to the light-receiving portion 16, in particular, enables a change in the diffuse reflected light 22 to be directly detected and therefore ensures that a defective surface portion such as a small break across which only a small change in the diffuse reflected light 22 is recognized can be detected with accuracy. That is, if the mask 18 is absent (see FIGS. 6(A) and 6(B)), both the specular reflected light 20 and the diffuse reflected light 22 are together received. Under this condition, it is difficult to detect a change in the diffuse reflected light 22 if the change is small relative to the quantity of the specular reflected light 20 received. In contrast, in the present embodiment shown in FIGS. 2(A) and 2(B), only a change in the quantity of the diffuse reflected light 22 is directly detected, so that a defective surface portion such as a small break across which only a small change in diffuse reflected light is recognized can be detected with accuracy. The mask 18 can be detached from the light-receiving portion 16 to enable inspection of products other than thermal-developable photosensitive material 10.

As described above, the specular reflected light 20 is cut out by the mask 18 attached to the light-receiving portion 16 to enable direct detection of a change in the quantity of the diffuse reflected light 22, thereby enabling a small defective surface portion across which only a small change in diffuse reflectance is recognized to be detected with accuracy. Consequently, it is possible to inspect even a thermal-developable photosensitive material having a high transmittance for defective surface portions by using the reflex-type optical sensor 12. The present invention is suitable for inspection of a photosensitive material having a transmittance of 20 to 50%, preferably 25 to 40% in particular.

Table 1 shows the results of an experiment in which a thermal-developable photosensitive material was inspected for defective surface portions in accordance with the above-described inspection principle according to an embodiment of the present invention. Table 1 further shows the results of evaluation of the performance in detecting the defective surface portions under different conditions with respect to use of two kinds of lasers: infrared (IR) laser and helium-neon (He—Ne) laser and the presence/absence of the mask.

An evaluation criterion symbol A indicates the result that all the defective surface portions were detected, a symbol B the result that all the defective surface portions were detected but there was an anxiety or a probability described in the table, and a symbol F the result that all or part of the defective surface portions were not detected.

TABLE 1

|  | Kind of laser | Detection output | Presence/ absence of mask | Performance/ operability |
| --- | --- | --- | --- | --- |
| Example 1 | IR laser | 1.0 V | Presence | A |
| Example 2 | IR laser | 0.7 V | Presence | B (There was an anxiety about a certain possibility of detection failure) |
| Example 3 | He—Ne laser | 1.0 V | Presence | B (There was an anxiety about fog) |
| Comparative Example 1 | IR laser | 1.0 V | Absence | F (Detection failure) |
| Comparative Example 2 | He—Ne laser | 0.7 V | Absence | F (Detection failure) |

As can be understood from Table 1, the performance in detecting the defective surface portions was improved when the mask 18 was attached. That is, in Comparative Examples 1 and 2 in which the mask 18 was not provided, the defective surface portions having lower diffuse reflectances were not detected. In contrast, in Examples 1 and 2 in which the mask 18 was attached, the corresponding defective surface portions were detected.

Table 2 shows the results of tests made to determine a preferable range of the detection output in accordance with the present invention.

TABLE 2

|  | Kind of laser | Detection output | Mask | Performance/operability |
| --- | --- | --- | --- | --- |
| Test 1 | IR laser | 0.5 V | Presence | F (There were many detection errors) |
| Test 2 | IR laser | 0.7 V | Presence | B (There were a certain number of instances of over-detection) |
| Test 3 | IR laser | 0.8 V | Presence | A |
| Test 4 | IR laser | 1.1 V | Presence | A |
| Test 5 | IR laser | 1.5 V | Presence | B (There was an anxiety about a certain possibility of detection failure) |
| Test 6 | IR laser | 1.7 V | Presence | F (Detection failure) |

As can be understood from Table 2, the detection output is preferably set within the range of 0.7 to 1.5 V and, more preferably, within the range of 0.8 to 1.1 V. When the detection output was in this range, the defective surface portions were detected with efficiency.

The kind of laser used in the present invention may be IR laser (830 nm) or He—Ne laser (633 nm). IR laser is particularly preferable. However, IR laser having a wavelength of 830 nm is not suitable for inspection of transparent photosensitive materials having photosensitivity to IR other than thermal-developable photosensitive materials. It is preferable to use as the light source a laser having a wavelength shifted by 20 nm or more, more preferably 50 nm or more, and furthermore preferably 100 nm or more from the maximum sensitivity wavelength of the color sensitivity of the photosensitive material whose defective surface portions are to be detected. The beam diameter and the number of times scanning is performed vary depending on the coating width and the speed of the product. However, it is preferable to select them so as to enable inspection through the entire surface.

According to the present invention, as described above, the mask 18 is attached to enable defective surface portions to be detected with accuracy. Also, since the mask 18 is used, the number of kinds of laser and the range of detection output are increased to facilitate selection of reflex-type optical sensor 12.

Embodiments of inspection apparatuses to which the above-described inspection principle is applied will be described.

Figure 3:
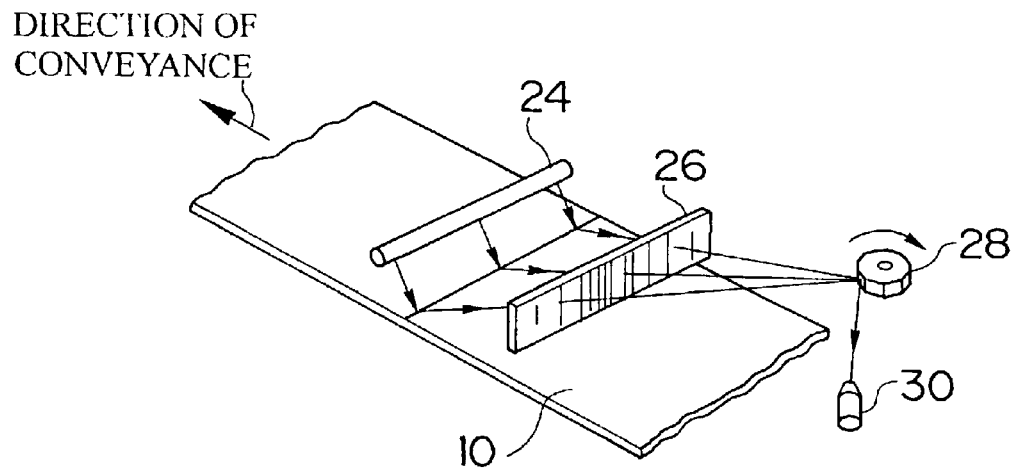
FIG. 3 is a perspective view of an embodiment of the reflex-type optical sensor.

FIG. 3 shows an inspection apparatus using a flying-image scanning method. As shown in FIG. 3, a light source 24 extending along a direction of width of the thermal-developable photosensitive material 10 is provided above the photosensitive material 10. Inspection light uniform along the width direction is emitted from the light source 24 toward the thermal-developable photosensitive material 10. The emitted inspection light is reflected by the thermal-developable photosensitive material 10, passes an optical filter 26, and reaches a rotary mirror 28. The optical filter 26 is formed by superposing neutral density (ND) filters having a thickness of about 100 μm for example and has such a transmittance distribution that the transmittance of its opposite side portions is higher than that of its central portion, and that the quantity of inspection light passed through the optical filter 26 is distributed generally uniformly along the width direction. This inspection light is reflected by the rotary mirror 28 to enter a light-receiving device 30. The inspection light is converted into an electrical signal by the light-receiving device 30. From a change in the output level of the electrical signal, a defective surface portion is detected. A mask (not shown) which cuts out specular reflected light is attached to the light-receiving device 30 so as to face the light-receiving surface of the light-receiving device 30 to enable the light-receiving device 30 to receive only diffuse reflected light. Therefore, even a defective surface portion across which only a small change in diffuse reflectance is recognized can be detected with efficiency.

Figure 4:
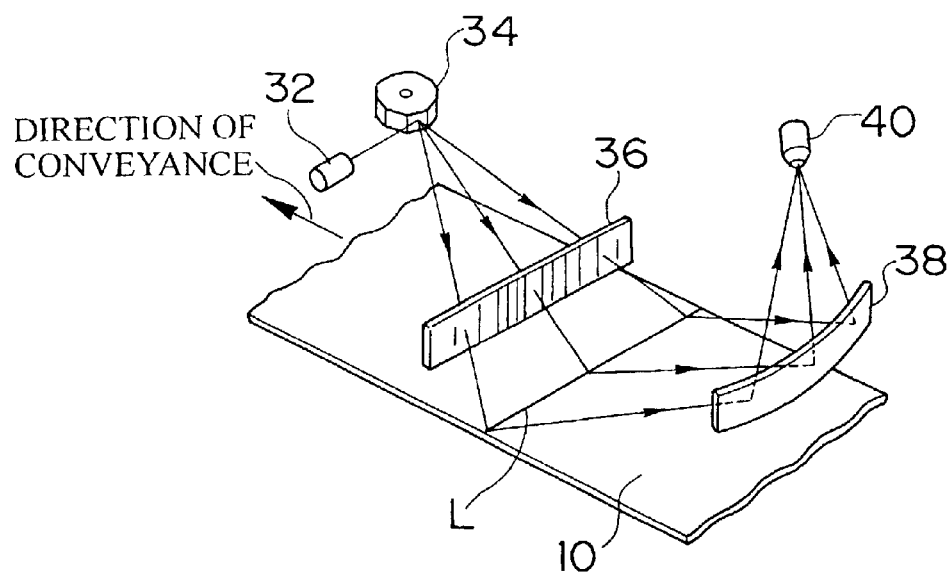
FIG. 4 is a perspective view of another embodiment of the reflex-type optical sensor.

FIG. 4 shows an inspection apparatus using a flying-spot scanning method. As shown in FIG. 4, a light source 32 and a rotary mirror 34 are provided above the thermal-developable photosensitive material 10. Inspection light emitted from the light source 32 is swung by the rotary mirror 34 for scanning along a scanning line L extending along the direction of width of the thermal-developable photosensitive material 10. An optical filter 36 is inserted between the rotary mirror 34 and the thermal-developable photosensitive material 10. The quantity of inspection light passed through the optical filter 36 is distributed uniformly along the width direction. Light reflected by the thermal-developable photosensitive material 10 is reflected by a concave mirror 38 to enter a light-receiving device 40. A mask (not shown) which cuts out specular reflected light is attached to the light-receiving device 40 so as to face the light-receiving surface of the light-receiving device 40 to enable the light-receiving device 40 to receive only diffuse reflected light. Therefore, even a defective surface portion across which only a small change in diffuse reflectance is recognized can be detected with efficiency.

The inspection apparatus constructed as described above may be operated by also using a transmission-type optical sensor to detect defective surface portions more efficiently.

Figure 5:
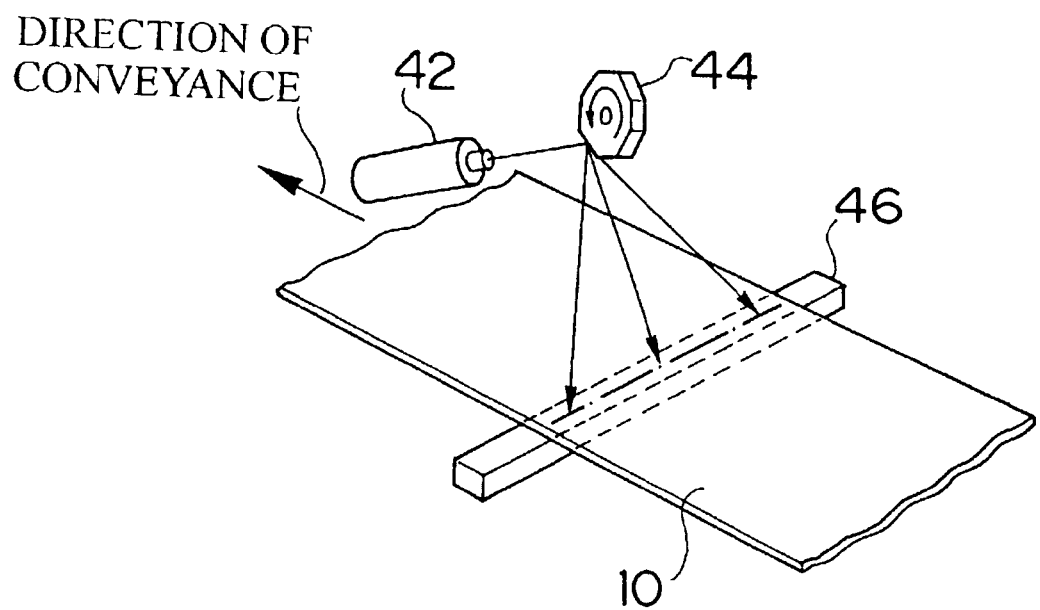
FIG. 5 is a perspective view of an embodiment of a transmission-type optical sensor.

As shown in FIG. 5, the transmission-type optical sensor is constituted by a light source 42 and a rotary mirror 44 provided above a thermal-developable photosensitive material 10, and a light-receiving device 46 provided below the thermal-developable photosensitive material 10. The light-receiving device 46 extends along a direction of width of the thermal-developable photosensitive material 10. Inspection light emitted from the light source 42 is swung by the rotary mirror 44 for scanning along a scanning line extending along the direction of width of the thermal-developable photosensitive material 10. Transmission light transmitted through the thermal-developable photosensitive material 10 enters the light-receiving device 46. From a change in the quantity of the transmission light, a defective surface portion is detected. Both the thus-arranged transmission-type optical sensor and the reflex-type optical sensor are used to enable a pin hole and a coating discontinuity portion, which are fatal defects in the photosensitive layer, to be detected with efficiency.

Next, a thermal-developable photosensitive material preferably used in the present invention will be described in detail below.

Organic silver salts that can be used in the present invention are relatively stable to light; however, when heated to 80° C. or above in the presence of an exposed photocatalyst (latent image of photosensitive silver halide and the like) and a reducer, they form silver images. The organic silver salts may be any organic substance containing a source that can reduce silver ions. Silver salts of organic acids, and particularly preferable are the silver salts of long-chain aliphatic carboxylic acids (of which the number of carbon atoms is 10 to 30, preferably 15 to 28). Preferable examples of the organic silver salts include silver behenate, silver arachidate, silver stearate, silver oleate, silver laurate, silver capronate, silver myristate, silver palmitate, and the mixture thereof. Of these organic silver salts, the use of an organic silver salt containing 75 mol % or more silver behenate is preferable in the present invention.

The form of the organic silver salts that can be used in the present invention is not specifically limited, and may be needle-like, bar-like, plate-like, and flake-like.

In the present invention, flake-like organic silver salts are preferable. The flake-like organic silver salts are herein defined as follows. When an organic silver salt is observed through an electron microscope, the form of a particle of the organic silver salt is approximately a rectangular parallelepiped, and when the edges of the rectangular parallelepiped are named as a, b, and c from the shortest edge (c may be the same as b), x is calculated from the shorter values a and b as follows:

$x=b/a$

Thus, x is calculated for about 200 particles, and when the average is called averaged value x (average), particles that satisfy the relationship of x(average)≧1.5 are defined as flake-shaped. Preferably, 30≧x(average)≧1.5, and more preferably, 20≧x(average)≧2.0. For reference, a needle-like particle is defined as 1≧x(average)≧1.5.

In a flake-like particle, a can be deemed as the thickness of a plate-like particle that has the face having sides b and c as the principal face. The average of a is preferably 0.01 μm to 0.23 μm, and more preferably 0.1 μm to 0.20 μm. The average of c/b is preferably 1 or more and 6 or less, more preferably 1.05 or more and 4 or less, further preferably 1.1 or more and 3 or less, and most preferably 1.1 or more and 2 or less.

The distribution of the particle sizes of the organic silver salt is preferably simple distribution. Simple distribution is the distribution when the percentage of the value obtained by dividing the standard deviations of the lengths of the minor axis and the major axis by the minor axis and the major axis, respectively, is 100% or below, more preferably 80% or below, and further preferably 50% or below. The form of the organic silver salt can be measured from the transmission electron microscope image of the dispersion of the organic silver salt. Another method for measuring simple distribution is a method to calculate the standard deviation of the volume-weighted average of the organic silver salt, and the percentage of the value obtained by dividing the standard deviation by the volume-weighted average (coefficient of variation) is preferably 100% or below, more preferably 80% or below, and further preferably 50% or below. The coefficient of variation can be obtained from the particle size (volume-weighted average diameter) obtained by radiating laser beams to the organic silver salt dispersed in a liquid, and obtaining the autocorrelation function for change in time of the wobble of the scattered light.

Known methods can be applied to the method for manufacturing an organic silver salt used in the present invention and to the method for dispersing it.

If a photosensitive silver salt is allowed to coexist when the organic silver salt is dispersed, fog increases and sensitivity lowers significantly; therefore, it is preferable not to substantially contain photosensitive silver salts when the organic silver salt is dispersed. In the present invention, the content of photosensitive silver salts in the aqueous dispersion is 0.1 mol % or less to 1 mole of the organic silver salt in the dispersion, and the photosensitive silver salts are not intentionally added.

In the present invention, although a photosensitive material can be manufactured by mixing an aqueous dispersion of an organic silver salt and an aqueous dispersion of a photosensitive silver salt, and the mixing ratio of the organic silver salt and the photosensitive silver salt can be selected depending on the purpose, the percentage of the photosensitive silver salt to the organic silver salt is preferably within a range between 1 mol % and 30 mol %, more preferably within a range between 3 mol % and 20 mol %, and most preferably within a range between 5 mol % and 15 mol %. Mixing two or more aqueous dispersions of organic silver salts and two or more aqueous dispersions of photosensitive silver salts is a method preferably used for the control of photographic performance.

Although any desired quantity of an organic silver salt can be used in the present invention, the quantity as silver is preferably 0.1 g/m$^2$ to 5 g/m$^2$, and more preferably 1 g/m$^2$ to 3 g/m$^2$.

It is preferable that the thermal-developable photosensitive material of the present invention contains a reducer for organic silver salts. The reducer for organic silver salts may be any substance (preferably an organic substance) that reduces silver ions to metallic silver.

In the present invention, a hindered phenol reducer and a bisphenol reducer are preferable as the reducer.

In the present invention, the quantity of the reducer is preferably 0.01 g/m$^2$ to 5.0 g/m$^2$, and more preferably 0.1 g/m$^2$ to 3.0 g/m$^2$. For one mole of silver on the surface having an image-forming layer, the content is preferably 5 mol % to 50 mol %, and more preferably 10 mol % to 40 mol %. The reducer is preferably contained in the image-forming layer.

The reducer may be contained in the coating liquid and therefore in the photosensitive material in any form, such as a dissolved form, an emulsified and dispersed form, and a dispersed fine solid particle form.

One of well-known emulsifying and dispersing methods is a method wherein a reducer is dissolved in oil, such as dibutyl phthalate, tricresyl phosphate, glyceryl triacetate, and diethyl phthalate; or an auxiliary solvent, such as ethyl acetate and cyclohexanone; and then the emulsion is mechanically formed.

Fine solid particle dispersing methods include a method wherein the powder of a reducer is dispersed in a suitable solvent, such as water, using a ball mill, a colloid mill, a vibrating ball mill, a sand mill, a jet mill, a roller mill, or ultrasonic waves to form a solid dispersion. In this time, a protective colloid (for example, polyvinyl alcohol) or a surfactant (for example, an anionic surfactant, such as sodium triisopropylnaphthalenesulfate (mixture of compounds wherein three isopropyl groups are bonded to different substitution sites)) may be used. The aqueous dispersion may contain an antiseptic agent (for example, benzoisothiazolinone sodium salt).

In the thermal-developable photosensitive material of the present invention, a phenol derivative is preferably used as a developing accelerator.

When the reducer in the present invention has an aromatic hydroxyl group (—OH), especially in the case of the above-described bisphenols, the combined used of a non-reducing compound having groups capable of forming a hydrogen bonds with these groups is preferable. Groups that form hydrogen bonds with hydroxyl or amino groups include phosphoryl, surfoxide, sulfonyl, carbonyl, amide, ester, urethane, ureido, tertiary amino, and nitrogen-containing aromatic groups. The preferable of these are compounds having a phophoryl group, a sulfoxide group, an amide group (having no >N—H groups, and blocked as >N—Ra (Ra is a substituent other than H)), a urethane group (having no >N—H groups, and blocked as >N—Ra (Ra is a substituent other than H)), and a ureido group (having no >N—H groups, and blocked as >N—Ra (Ra is a substituent other than H)).

Halogen components in photosensitive silver halides used in the present invention are not specifically limited, and silver chloride, silver chlorobromide, silver bromide, silver iodobromide, and silver iodochlorobromide can be used. Of these, silver bromide and silver iodobromide are preferable. The halogen components in a silver halide particle may be evenly distributed, may change stepwise, or may change continuously. Silver halide particles having a core-and-shell structure may also be preferably used. The core-and-shell structure that can be used is preferably a two-layer to five-layer structure, and more preferably a two-layer to four-layer structure. The technique for allowing silver bromide to be locally present on the surfaces of silver chloride or silver chlorobromide particles can also be preferably used.

Methods for forming photosensitive silver halide are well known to the skilled in the art. Specifically, a photosensitive silver halide is formed by adding a silver-providing compound and a halogen-providing compound in a solution of gelatin or other polymers, and then it is mixed with an organic silver salt.

It is preferably that the particle size of the light sensitive silver halide is small for inhibiting clouding after forming images. Specifically, it is preferably 0.2 $\mu$m or smaller, more preferably 0.01 $\mu$m or larger and 0.15 $\mu$m or smaller, and most preferably 0.02 $\mu$m or larger and 0.12 $\mu$m or smaller.

The term "particle size" used herein is the diameter when the projected area of a silver halide particle (in the case of plate-like particle, the projected area of the major face) is converted to the circular image of the identical area.

The shapes of the silver halide particles include cubic, octahedral, tabular, spherical, rod-like, and potato-like. In the present invention, cubic particles are particularly preferable. Silver halide particles having rounded corners can also be preferably used. The plane index (Miller index) of the outer surfaces of photosensitive silver halide particles is not specifically limited; however, it is preferable that the percentage of {100} planes, which has a high spectral sensitization efficiency when spectral sensitization dyes are adsorbed, is high. The percentage is preferably 50% or more, more preferably 65% or more, and most preferably 80% or more. The Miller index, the percentage of {100} planes, can be obtained using the method that utilizes the adsorption dependency of {111} planes and {100} planes in the adsorption of the sensitizing dyes.

In the present invention, silver halide particles having a hexacyano-metal complex existing on the outermost surface thereof are preferable. The hexacyano-metal complexes include $[Fe(CN)_6]^{4-}$, $[Fe(CN)_6]^{3-}$, $[Ru(CN)_6]^{4-}$, $[Os(CN)_6]^{4-}$, $[Co(CN)_6]^{3-}$, $[Rn(CN)_6]^{3-}$, $[Ir(CN)_6]^{3-}$, $[Cr(CN)_6]^{3-}$, and $[Re(CN)_6]^{3-}$. In the present invention, a hexacyano-iron complex is preferable.

Since hexacyano-metal complexes are present in the form of ions in the aqueous solutions, the countercations are not important; however, the use of alkali-metal ions, such as sodium ions, potassium ions, rubidium ions, cesium ions, and lithium ions; ammonium ions; alkyl ammonium ions (for example, tetramethyl ammonium ions, tetraethyl ammonium ions, tetrapropyl ammonium ions, and tetra (n-butyl) ammonium ions), which are miscible with water and suitable for sedimentation of silver halide emulsions, is preferable.

The hexacyano-metal complexes can be added in the form of water, a mixture with a suitable organic solvent miscible with water (for example, alcohols, ethers, glycols, ketones, esters, amides, and the like), or gelatin.

The quantity of the hexacyano-metal complex added to 1 mole of silver is preferably $1 \times 10^{-5}$ mole or more and $1 \times 10^{-2}$ mole or less, and more preferably $1 \times 10^{-4}$ mole or more and $1 \times 10^{-3}$ mole or less.

In order to allow the hexacyano-metal complex to be present on the outermost surfaces of silver halide particles, the hexacyano-metal complex is directly added after the addition of the aqueous solution of silver nitrate used for forming particles is completed, and before the charging step up to the chemical sensitizing step for chalcogen sensitization, such as sulfur sensitization, selenium sensitization, and tellurium sensitization, or noble-metal sensitization, such as gold sensitization, is completed, that is, during the water-washing step, the dispersing step, or chemical sensitizing step. In order not to grow the silver halide particles, it is preferable to add the hexacyano-metal complex promptly after the formation of particles, and to add before the completion of the charging step.

The addition of the hexacyano-metal complex may be started after 96% by mass of the total quantity of silver nitrate is added for forming particles, and preferably after 98% by mass is added, and more preferably after 99% by mass is added.

If the hexacyano-metal complex is added after the addition of the aqueous solution of silver nitrate immediately before the completion of the formation of particles, the hexacyano-metal complex can be adsorbed on the outermost surfaces of the silver halide particles, and most of the hexacyano-metal complex reacts with silver ions to form hardly soluble salts. Since the silver salt of hexacyano iron (II) is a harder soluble salt than AgI, redissolution by fine particles can be prevented, and the particles of silver halide having a small particle size can be manufactured.

The photosensitive silver halide particles of the present invention can contain metals or metal complexes of groups 8 to 10 in the periodic table (from group 1 to group 18). The preferable metals in metals or metal complexes of groups 8 to 10 are rhodium, ruthenium, and iridium. These metal complexes may be used alone, or in combination of two or more metals of the same group or of different groups. The content is preferably within a range between $1 \times 10^{-9}$ mole and $1 \times 10^{-3}$ mole to 1 mole of the silver.

Various types of gelatin can be used as the gelatin contained in the photosensitive silver halide emulsion used in the present invention. In order to maintain the dispersion of the photosensitive silver halide emulsion in an organic-silver-salt-containing coating liquid, the use of a low-molecular-weight gelatin of a molecular weight of 500 to 60,000 is preferable. Although such a low-molecular-weight gelatin may be used when the particles are formed, or dispersed after desalination treatment, it is preferable to use when the particles are dispersed after desalination treatment.

As a sensitizing dye that can be used in the present invention, a sensitizing dye that can spectrally sensitize silver halide particles in a desired wave-length region when adsorbed on the silver halide particles, and that has a spectral sensitivity commensurate with the spectral properties of the exposing light source can be chosen advantageously. These sensitizing dyes may be used alone, or may be used in combination of two or more dyes. In the present invention, the time for adding the sensitizing dye in the silver halide emulsion is preferably after the desalination step up to application, and more preferably after the desalination step and before starting chemical aging.

Although the quantity of the sensitizing dye in the present invention can be any desired quantity to meet the properties of sensitivity or fog, the quantity for 1 mole of the silver halide in the photosensitive layer is preferably $10^{-6}$ mole to 1 mole, and more preferably $10^{-4}$ mole to $10^{-1}$ mole.

In order to improve the efficiency of spectral sensitization, a strong color sensitizer can be used in the present invention.

It is preferable that the photosensitive silver halide particles in the present invention are chemically sensitized by sulfur sensitization, selenium sensitization, or tellurium sensitization. Compounds preferably used in sulfur sensitization, selenium sensitization, and tellurium sensitization are well known to those skilled in the art. Particularly in the present invention, tellurium sensitization is preferable.

In the present invention, chemical sensitization can be performed at any time after the formation of particles and before application, and specifically, it can be performed after desalination and (1) before spectral sensitization, (2) at the same time of spectral sensitization, (3) after spectral sensitization, and (4) immediately before application. In particular, it is preferable that chemical sensitization is performed after spectral sensitization.

Although the quantity of sulfur, selenium, and tellurium sensitizers used in the present invention varies depending on silver halide particles used, or the conditions of chemical aging, the quantity for 1 mole of the silver halide is usually $10^{-8}$ mole to $10^{-2}$ mole, and preferably $10^{-7}$ mole to $10^{-3}$ mole. Although the conditions of chemical sensitization in the present invention are not specifically limited, the pH is preferably 5 to 8, the pAg is preferably 6 to 11, and the temperature is preferably 40° C. to 95° C.

To the silver halide emulsion used in the present invention, a thiosulfonate compound may be added.

The photosensitive silver halide emulsion in the photosensitive material used in the present invention can be used alone, or two or more photosensitive silver halide emulsions (for example, of different average particle sizes, different halogen compositions, different crystal habits, or different conditions of chemical sensitization) can be used in combination. The use of a plurality of photosensitive silver halides of different sensitivities can control the tone. The difference in sensitivity of each emulsion is preferably 0.2 log E or more.

The quantity of the photosensitive silver halide in terms of the quantity of coating silver for 1 m² of the photosensitive material is preferably 0.03 g/m² to 0.6 g/m², more preferably 0.07 g/m² to 0.4 g/m², and most preferably 0.05 g/m² to 0.3 g/m². To 1 mole of the organic silver salt, the quantity of the photosensitive silver halide is preferably 0.01 mole or more and 0.5 mole or less, and more preferably 0.02 mole or more and 0.3 mole or less.

The methods and conditions for mixing the photosensitive silver halide and the organic silver salt separately prepared include a method for mixing the prepared silver halide particles and the organic silver salt using a high-speed agitator, a ball mill, a sand mill, a colloid mill, a vibrating mill, or a homogenizer; or a method for mixing the prepared photosensitive silver halide in some timing during the preparation of the organic silver salt; however, the method is not limited to a specific method as long as the effect of the present invention is obviously obtained. Mixing two or more aqueous dispersions of organic silver salt and two or more aqueous dispersions of photosensitive silver salt is a preferable method for controlling photographic properties.

Although the time for adding the silver halide in a coating liquid for image forming layers in the present invention is 180 minutes before application to immediately before application, preferably 60 minutes to 10 seconds before application, a method and a condition for mixing are not specifically limited as long as the effect of the present invention is obviously obtained. Specific mixing methods include a method of mixing in a tank wherein the average retention time calculated from the flow rate and the quantity to the coater is controlled to a desired time; or a method to use a static mixer.

The binder of an organic-silver-salt-containing layer of the present invention may be any polymer, and preferable binders are transparent or translucent, and are generally colorless. They include natural resins, polymers, and copolymers; synthetic resins, polymers, and copolymers; and other media forming films, for example, gelatins, rubbers, polyvinyl alcohols, hydroxyethyl cellulose, cellulose acetate, cellulose acetate butylate, polyvinyl pirrolidone, casein, starch, polyacrylate, polymethyl methacrylate, polyvinyl chloride, polymethacrylate, styrene-maleic anhydride copolymers, styrene-acrylonitrile copolymers, styrene-butadiene copolymers, polyvinyl acetal (for example, polyvinyl methylal and polyvinyl butylal), polyesters, polyurethane, phenoxy resins, polyvinylidene chloride, polyepoxide, polycarbonate, polyvinyl acetate, polyolefins, cellulose esters, and polyamides. The binders may also be formed by coating from water, organic solvents, or emulsions.

In the present invention, the glass transition temperature of the binder for the layer containing the organic silver salt is preferably 10° C. or above and 80° C. or below (hereinafter also referred to as "high Tg binder"), more preferably 20° C. to 70° C., and most preferably 23° C. or above and 65° C. or below.

The Tg herein was calculated using the following equation.

$$1/Tg = \Sigma(Xi/Tgi)$$

Here, n monomer components, from i=1 to n, are assumed to copolymerize in the polymer. Xi is the mass percentage of the i-th monomer ($\Sigma Xi=1$), and Tgi is the glass transition temperature (Kelvin) of the homopolymer of the i-th monomer. $\Sigma$ is the sum from i=1 to n. The values of the glass transition temperature of homopolymer of each monomer (Tgi) were taken from J. Brandrup and E. H. Immergurt, Polymer Handbook (3rd Edition) (Wiley-Interscience, 1989).

The polymers constituting the binder may be used alone, or used in combination of two or more as required. A polymer having a glass transition temperature of 20° C. or above may be combined with a polymer having a glass transition temperature below 20° C. When two or more polymers having different Tg are blended, it is preferable that the mass average Tg falls in the above-described range.

In the present invention, the performance is improved when the organic-silver-salt-containing layer is formed by coating with a coating liquid containing a solvent whose 30% by mass or more is water, and drying; furthermore, when the binder of the organic-silver-salt-containing layer is soluble or dispersible in a water-based solvent (aqueous solvent); and particularly when the binder is composed of a polymer latex having an equilibrium moisture content at 25° C. and 60% RH of 2% by mass or less. The most preferable aspect is prepared so that the ion conductivity becomes 2.5 mS/cm or below. The methods for preparing such an aspect include purification treatment of the synthesized polymer using a membrane having an isolating function.

The water-based solvent wherein the polymer is soluble or dispersible used herein is water, or the mixture of water and 70% by mass or less water-miscible organic solvent. Water-miscible organic solvents include, for example, alcohols, such as methyl alcohol, ethyl alcohol, and propyl alcohol; cellosolves, such as methyl cellosolve, ethyl cellosolve, and butyl cellosolve; ethyl acetate; and dimethyl formamide.

In the case of a system wherein the polymer is not thermodynamically dissolved, and is present in a so-called dispersed state, the term of a water-based solvent is used here.

The "equilibrium moisture content at 25° C. and 60% RH" is represented by the following equation using the mass of the polymer W1 in a humidity-controlled equilibrium under an atmosphere of 25° C. and 60% RH, and the mass of the polymer W0 in the absolute dry condition at 25° C.

Equilibrium moisture content at 25° C. and 60% RH={(W1−W0)/W0}×100(% by mass)

The definition and the measuring method of moisture content can be referred to, for example, Polymer Engineering Seminar 14, Methods for Testing Polymers (Society of Polymer Science, Japan, Chijin Shokan).

The equilibrium moisture content at 25° C. and 60% RH of the binder polymer of the present invention is preferably 2% by mass or less, more preferably 0.01% by mass or more and 1.5% by mass or less, and most preferably 0.02% by mass or more and 1% by mass or less.

In the present invention a polymer that is dispersible in a water-based solvent is particularly preferable. Examples of dispersed states include a latex wherein fine particles of a hydrophobic polymer insoluble in water are dispersed, and a dispersion of polymer molecules in a molecular state or in a micelle state, both of which are preferable. The average particle diameter of the dispersed particles is preferably within a range between 1 nm and 50,000 nm, and more preferably within a range between 5 nm and 1,000 nm. The particle diameter distribution of the dispersed particles is not specifically limited, and the dispersed particles may have a wide particle diameter distribution or a monodisperse particle diameter distribution.

In the present invention, preferred aspects of polymers dispersible in water-based solvents include hydrophobic polymers, such as acrylic polymers, polyesters, rubber (for example, SBR resin), polyurethane, polyvinyl chloride, polyvinyl acetate, polyvinylidene chloride, and polyolefins. These polymers may be straight-chain polymers, branched polymers or cross-linked polymers; may be homopolymers wherein a single type of monomers are polymerized; or may be copolymers wherein two or more types of monomers are polymerized. The copolymers may be random copolymers, or may be block copolymers. The molecular weight (number average molecular weight) of these polymers is 5,000 to 1,000,000, preferably 10,000 to 200,000. If the molecular weight is too low, the mechanical strength of the emulsion layer is insufficient; and if the molecular weight is too high, the film forming capability becomes poor.

Specific examples of preferable latexes are listed below. The list shows material monomers, the unit of values in parentheses is % by mass, and molecular weights are number average molecular weights. In the case of polyfunctional monomers, since the concept of molecular weight cannot be applied because they form cross-linked structures, they are described as "cross-linkable", and the description of molecular weights is omitted. Tg denotes glass transition temperature.

P-1; -MMA (70)-EA (27)-MAA (3)-latex (molecular weight: 37,000)
P-2; -MMA (70)-2EHA (20)-St (5)-AA (5)-latex (molecular weight: 40,000)
P-3; -St (50)-Bu (47)-MAA (3)-latex (cross-linkable)
P-4; -St (68)-Bu (29)-AA (3)-latex (cross-linkable)
P-5; -St (71)-Bu (26)-AA (3)-latex (cross-linkable, Tg 24° C.)
P-6; -St (70)-Bu (27)-IA (3)-latex (cross-linkable)
P-7; -St (75)-Bu (24)-AA (1)-latex (cross-linkable)
P-8; -St (60)-Bu (35)-DVB (3)-MAA (2)-latex (cross-linkable)
P-9; -St (70)-Bu (25)-DVB (2)-AA (3)-latex (cross-linkable)
P-10; -VC (50)-MMA (20)-EA (20)-AN (5)-AA (3)-latex (molecular weight: 80,000)
P-11; -VDC (85)-MMA (5)-EA (5)-MAA (5)-latex (molecular weight: 67,000)
P-12; -Et (90)-MMA (10)-latex (molecular weight: 12,000)
P-13; -St (70)-2EHA (27)-AA (3)-latex (molecular weight: 130,000)
P-14; -MMA (63)-EA (35)-AA (2)-latex (molecular weight: 33,000)
P-15; -St (70.5)-Bu (26.5)-AA (3)-latex (cross-linkable, Tg 23° C.)
P-16; -St (69.5)-Bu (27.5)-AA (3)-latex (cross-linkable, Tg 20.5° C.)

Abbreviations in the above-described structures denote the following monomers: MMA: methyl methacrylate, EA: ethyl acrylate, MAA: methacrylic acid, 2EHA: 2-ethylhexyl acrylate, St: styrene, Bu: butadiene, AA: acrylic acid, DVB: divinyl benzene, VC: vinyl chloride, AN: acrylonitrile, VDC: vinylidene chloride, Et: ethylene, IA: itaconic acid.

The above-described polymer latexes are also sold in the market, and the following polymers are commercially available. Examples of acrylic polymers include Cevian A-4635, 4718, and 4601 (Daicel Chemical Industries) and Nipol Lx 811, 814, 821, 820, and 857 (ZEON Corporation); examples of polyesters include FINETEX ES 650, 611, 675, and 850 (Dainippon Ink and Chemicals, Inc.) and WD-size and WMS (Eastman Chemical); examples of polyurethane include HYDRAN AP 10, 20, 30, and 40 (Dainippon Ink and Chemicals, Inc.); examples of rubbers include LACSTAR 7301K, 3307B, 4700H, and 7132C (Dainippon Ink and Chemicals, Inc.) and Nipol Lx 416, 410, 438C, and 2507 (ZEON Corporation); examples of polyvinyl chloride include G351 and G576 (ZEON Corporation); examples of polyvinylidene chloride include L502 and L513 (Asahi Kasei); and examples of polyolefins include Chemipearl S120 and SA100 (Mitsui Chemicals).

These polymer latexes may be used alone, or may be used in combination of two or more as required.

The polymer latex preferably used in the present invention is latex of a styrene-butadiene copolymer. The mass ratio of styrene monomer units to butadiene monomer units in the styrene-butadiene copolymer is preferably 40:60 to 95:5. The proportion of styrene monomer units and butadiene monomer units in the copolymer is preferably 60% by mass to 99% by mass. The preferable molecular weight range is the same as described above.

Latexes of styrene-butadiene copolymers preferably used in the present invention include the above-described P-3 to P-8, P-14, P-15, commercially available LACSTAR-3307B, 7132C, and Nipol Lx 416.

In the organic-silver-salt-containing layer of the photosensitive material of the present invention, hydrophilic polymers, such as gelatin, polyvinyl alcohol, methylcellulose, hydroxypropyl cellulose, and carboxymethyl cellulose may be added as required. The content of these hydrophilic polymers in the total quantity of binders in the organic-silver-salt-containing layer is preferably 30% by mass or less, and more preferably 20% by mass or less.

The organic-silver-salt-containing layer (image forming layer) of the present invention is preferably formed from polymer latex. The mass ratio of the total quantity of the binder to the organic silver salt in the organic-silver-salt-containing layer is within a range between 1/10 and 10/1, preferably 1/5 and 4/1.

Such an organic-silver-salt-containing layer is normally a photosensitive layer (emulsion layer) containing photosensitive silver halide, which is a photosensitive silver salt, and in this case, the mass ratio of total binders to the silver halide is within a range between 400 and 5, preferably 200 to 10.

The total quantity of the binder in the image-forming layer of the present invention is within a range between 0.2 g/m$^2$ and 30 g/m$^2$, preferably between 1 g/m$^2$ and 15 g/m$^2$. In the image-forming layer of the present invention, a cross-linking agent for cross-linking, and a surfactant for improving coating properties may be added.

In the present invention, the solvent (here, a solvent and a dispersant are collectively referred to as solvent for simplification) in the coating liquid for the organic-silver-salt-containing layer of the photosensitive layer in the present invention is preferably a water-based solvent containing 30% by mass or more water. The components other than water may be any optional water-miscible organic solvents, such as methyl alcohol, ethyl alcohol, isopropyl alcohol, methyl cellosolve, ethyl cellosolve, dimethyl formamide and ethyl acetate. The water content in the solvent of the coating liquid is preferably 50% by mass or more, and more preferably 70% by mass or more. The preferable examples of solvent compositions are water, water/methyl alcohol=90/10, water/methyl alcohol=70/30, water/methyl alcohol/dimethyl formamide=80/15/5, water/methyl alcohol/ethyl cellosolve=85/10/5, and water/methyl alcohol/isopropyl alcohol=85/10/5 (unit: % by mass).

The organic polyhalogen compounds preferably used in the present invention will specifically be described below. The preferable polyhalogen compounds are compounds represented by the following general formula (III).

Q—(Y)n—C(Z1)(Z2)X            General formula (III)

In general formula (III), Q represents an alkyl group, aryl group, or heterocyclic group; Y represents a divalent coupling group; n represents 0 or 1; Z1 and Z2 represent halogen atoms; and X represents a hydrogen atom or an electron-attracting group. In general formula (III), Q is preferably a phenyl group substituted by an electron-attracting group whose Hamett substituent constant σp is positive. The Hamett substituent constant is described in Journal of Medicinal Chemistry, 1973, Vol. 16, No. 11, pp. 1207–1216. Such electron-attracting groups include, for example, halogen atoms (fluorine atom (σp value: 0.06), chlorine atom (σp value: 0.23), bromine atom (σp value: 0.23), iodine atom (σp value: 0.18)), trihalomethyl groups (tribromomethyl (σp value: 0.29), trichloromethyl (σp value: 0.33), trifluoromethyl (σp value: 0.54)), cyano group (σp value: 0.66), nitro group (σp value: 0.78), aliphatic aryl or heterocyclic sulfonyl groups (for example, methane sulfonyl (σp value: 0.72)), aliphatic aryl or heterocyclic acyl groups (for example, acetyl (σp value: 0.50), benzoyl (σp value: 0.43)), alkynyl groups (for example, C≡CH (σp value: 0.23)), aliphatic aryl or heterocyclic oxycarbonyl groups (for example, methoxy carbonyl (σp value: 0.45), phenoxy carbonyl (σp value: 0.44)), carbamoyl group (σp value: 0.36), sulfamoyl groups (σp value: 0.57), sulfoxide groups, heterocyclic groups, and phosphoryl groups. The σp value is preferably within a range between 0.2 and 2.0, more preferably within a range between 0.4 and 1.0. Particularly preferable electron-attracting groups are carbamoyl, alkoxycarbonyl, alkylsulfonyl, and alkylphosphoryl groups, of which the most preferable is the carbamoyl group.

X represents preferably an electron-attracting group, more preferably a halogen atom, an aliphatic aryl or heterocyclic sulfonyl group, an aliphatic aryl or heterocyclic acyl group, an aliphatic aryl or heterocyclic oxycarbonyl group, a carbamoyl group, and a sulfamoyl group, and particularly preferably a halogen atom. Among halogen atoms, a chlorine atom, bromine atom, and iodine atom are preferable; a chlorine atom and bromine atom are more preferable; and a bromine atom is most preferable.

Y represents preferably —C(=O)—, —SO—, or —SO$_2$—, more preferably —C(=O)— or —SO$_2$—, and most preferably —SO$_2$—. n represents 0 or 1, preferably 1.

In the present invention, the methods for containing an anti-fog agent in the photosensitive material include the method described in the above-described method for containing the reducer, and the addition of fine solid particles is also preferable for the organic polyhalogen compound.

The thermal-developable photosensitive material of the present invention may contain an azolium salt for the purpose of preventing fog. Although the azolium salt can be added to any positions in the photosensitive material, addition to the layer on the surface having the photosensitive layer is preferable, and addition to the organic-silver-salt-containing layer is more preferable. Although the azolium salt can be added in any steps for the preparation of the coating liquid, and when it is added to the organic-silver-salt-containing layer, it can be added in any steps from the time for the preparation of the organic silver salt to the preparation of the coating liquid, and preferably the time after the preparation of the organic silver salt to immediately before coating. The azolium salt may be added in any forms, such as powder, a solution, and a dispersion of fine particles. It may also be added as a solution whereto other additives, such as a sensitizing dye, a reducer, and toning agent, are added. In the present invention, although the quantity of the azolium salt to be added may be optional, it is preferably $1\times10^{-6}$ mole or more and 2 moles or less, and more preferably $1\times10^{-3}$ mole or more and 0.5 moles or less to 1 mole of silver.

In the present invention, a mercapto compound, a disulfide compound, and a thion compound may be contained for inhibiting, accelerating, or controlling development; for improving the efficiency of spectral sensitization; and for improving storage stability before and after development. A mercapto-substituted heterocyclic aromatic compound is preferable.

In the thermal-developable photosensitive material of the present invention, the addition of a toning agent is preferable. As toning agents, particularly preferable are phthaladinones (phthaladinone, phthaladinone derivatives, or metal salts; for example, 4-(1-naphthyl) phthaladinone, 6-chlorophthaladinone, 5,7-dimethoxyphthaladinone, and 2,3-dihydro-1,4-phthaladinedione); the combination of phthaladinones and phthalates (for example, phthalic acid, 4-methyl phthalic acid, 4-nitro phthalic acid, diammonium phthalate, sodium phthalate, potassium phthalate, and tetrachloro phtalic anhydride); phthaladines (phthaladine, phthaladine derivatives, or metal salts; for example, 4-(1-naphthyl) phthaladine, 6-isopropyl phthaladine, 6-t-butyl phthaladine, 6-chloro phthaladine, 5,7-dimethoxy phthaladine, and 2,3-dihydro phthaladine); and the combination of phthaladines and phthalates. Of these, the combination of phthaladines and phthalates is most preferable.

In order to use formic acid or a formate as a strong fogging substance, it is preferably contained in the side having an image-forming layer that contains the photosensitive silver halide in a quantity of 5 mmol or less for 1 mole of silver, more preferably 1 mmol or less.

When an ultra-high contrast agent is used in the thermal-developable photosensitive material of the present invention, it is preferable to use in combination with an acid or the salt thereof formed by hydrating diphosphorus pentaoxide. The acids or the salts thereof formed by hydrating diphosphorus pentaoxide include metaphosphoric acid (metaphosphorates), pyrophosphoric acid (pyrophosphorates), orthophosphoric acid (orthophosphorates), triphosphoric acid (triphosphorates), tetraphosphoric acid (tetraphosphorates), and hexametaphosphoric acid (hexametaphosphorates). Particularly preferable acids or the salts thereof formed by hydrating diphosphorus pentaoxide are orthophosphoric acid (orthophosphorates), and hexametaphosphoric acid (hexametaphosphorates). Specific salts include sodium orthophosphorate, dihydrogen sodium orthophosphorate, sodium hexametaphosphorate, and ammonium hexametaphosphorate.

Although the quantity (coating quantity for 1 m$^2$ of the photosensitive material) of acids or the salts thereof formed by hydrating diphosphorus pentaoxide may be as desired depending on the performance, such as sensitivity and fog, it is preferably 0.1 mg/m$^2$ to 500 mg/m$^2$, and more preferably 0.5 mg/m$^2$ to 100 mg/m$^2$.

The thermal-developable photosensitive material of the present invention may have a surface-protecting layer for the purpose of preventing the adherence of the image-forming layer. The surface-protecting layer may be of a single layer, or may be of multiple layers.

Although gelatin is preferably used for the binder of the surface-protecting layer of the present invention, it is also preferable to use or to combine polyvinyl alcohol (PVA). Gelatin that can be used include inert gelatin (for example, Nitta Gelatin 750) and phthalated gelatin (for example, Nitta Gelatin 801). PVA such as fully saponified PVA-105, partially saponified PVA-205, PVA-335, and modified polyvinyl alcohol MP-203 (KURARAY) are preferably used. The quantity of polyvinyl alcohol coating as the protecting layer (per layer) (per 1 m$^2$ of the support) is preferably 0.3 g/m$^2$ to 4.0 g/m$^2$, and more preferably 0.3 g/m$^2$ to 2.0 g/m$^2$.

Particularly, when the thermal-developable photosensitive material of the present invention is used for printing, wherein change in dimensions raises problems, the use of polymer latex in the surface-protecting layer or the backing layer is preferable. Specifically, the polymer latexes include a latex of methyl methacrylate (33.5% by mass)/ethyl acrylate (50% by mass)/methacrylic acid (16.5% by mass) copolymer; a latex of methyl methacrylate (47.5% by mass)/butadiene (47.5% by mass)/itaconic acid (5% by mass) copolymer; a latex of ethyl acrylate/metacrylic acid copolymer; a latex of methyl methacrylate (58.9% by mass)/2-etylhexyl acrylate (25.4% by mass)/styrene (8.6% by mass)/2-hydroxyethyl methacrylate (5.1% by mass)/acrylic acid (2.0% by mass) copolymer; and a latex of methyl methacrylate (64.0% by mass)/ styrene (9.0% by mass)/butyl acrylate (20.0% by mass)/2-hydroxyethyl methacrylate (5.0% by mass)/acrylic acid (2.0% by mass) copolymer. The content of the polymer latex for surface-protecting layer is preferably 10% by mass to 90% by mass of the total binder, more preferably 20% by mass to 80% by mass.

The quantity of the total binders (including water-soluble polymers and latex polymers) of the surface-protecting layer (per layer) (per 1 m$^2$ of the support) is preferably 0.3 g/m$^2$ to 5.0 g/m$^2$, and more preferably 0.3 g/m$^2$ to 2.0 g/m$^2$.

The temperature in the preparation of the coating liquid for the image-forming layer in the present invention is 30° C. or above and 65° C. or below, preferably 35° C. or above and below 60° C., and more preferably 35° C. or above and 55° C. or below. It is also preferable that the temperature of the coating liquid for the image-forming layer immediately after the addition of polymer latex is maintained at 30° C. or above and 65° C. or below.

The image-forming layer of the present invention is composed of one or more layer on the support. When it is composed of one layer, the layer comprises an organic silver salt, photosensitive silver halide, a reducer, and a binder, and as required, contains additional materials, such as a toning agent, covering additives and other auxiliary agents. When it is composed of two or more layers, the first image-forming layer (normally the layer contacting the support) must contain an organic silver salt and photosensitive silver halide, and the second image-forming layer or both layers must contain other several components. The constitution of a multicolor photosensitive thermal-developable photographic material may contain the combination of these two layers for each color, and all the components may be contained in a single layer. In the case of a multi-dye multicolor photosensitive thermal-developable photographic material, each emulsion layer is separated from each other and maintained by using a functional or non-functional barrier layer between each photosensitive layer.

Various dyes or pigments (for example, C. I. Pigment Blue 60, C. I. Pigment Blue 64, and C. I. Pigment Blue 15:6)

can be used in the photosensitive layer of the present invention from the pint of view of improving color tone, preventing the occurrence of interference fringes in exposing a laser beam, and preventing irradiation.

In the thermal-developable photosensitive material of the present invention, an anti-halation layer can be provided on the side of photosensitive layer remote from the light source.

A thermal-developable photosensitive material has generally non-photosensitive layers in addition to a photosensitive layer. Non-photosensitive layers can be classified according to the location thereof into (1) a protecting layer provided on the photosensitive layer (remote side from the support), (2) an intermediate layer provided between a plurality of photosensitive layers or between the photosensitive layer and the protecting layer, (3) a primer layer provided between the photosensitive layer and the support, and (4) a backing layer provided on the side opposite to the photosensitive layer. A filter layer is provided on the photosensitive layer as the layer (1) or (2). The anti-halation layer is provided on the photosensitive layer as the layer (3) or (4).

The anti-halation layer contains an anti-halation dye having absorption in the exposure wavelength. When the exposure wavelength is in the infrared region, an infrared absorbing dye can be used, and in this case, the dye that has no absorption in the visible region is preferable.

If halation is prevented using a dye having absorption in the visible region, it is preferable that the color of the dye does not substantially remain after forming images, a means to vanish the color with the heat of thermal development is used, and in particular, a thermally achromatizing dye and a base precursor are added to a non-photosensitive layer to function as an anti-halation layer.

The quantity of the achromatizing dye is determined according to the use of the dye. In general, it is used in a quantity that the optical density (absorbance) measured by the objective wavelength exceeds 0.1. The optical density is preferably 0.2 to 2. The quantity of the dye for obtaining such an optical density is generally approximately 0.001 $g/m^2$ to 1 $g/m^2$.

When the dye is achromatized, the optical density after thermal development can be lowered to 0.1 or less. Two or more achromatizing dyes may be used in combination in a thermally achromatizing recording material or a thermal-developable photosensitive material. Similarly, two or more base precursors may be used in combination.

In thermal achromatizing using such achromatizing dyes and base precursors, the combination use of a substance that lowers the melting point by 3 degrees or more by mixing with a base precursor (for example, diphenylsulfone and 4-chloroprene (phenyl) sulfide) is preferable from the point of view of thermal achromatizing.

In the present invention, for the purpose of improving change by aging of the silver color tone and the images, a colorant having an absorption maximum at 300 nm to 450 nm can be added.

Such a colorant is normally added within a range between 0.1 $mg/m^2$ and 1 $mg/m^2$, and the layer for the addition of the colorant is preferably the back layer provided opposite to the photosensitive layer.

The thermal-developable photosensitive material in the present invention is preferably a one-sided photosensitive material having at least one photosensitive layer containing a silver halide emulsion on one side of the support, and having a backing layer on the other side.

In the present invention, it is preferable to add a mat agent for improving conveying properties. The quantity of the mat agent coating for 1 $m^2$ of the photosensitive material is preferably 1 $mg/m^2$ to 400 $mg/m^2$, and more preferably 5 $mg/m^2$ to 300 $mg/m^2$.

Although any mat degree of the emulsion surface is optional unless stardust defects occur, the Peck flatness is preferably 30 seconds or more and 2,000 seconds or less, and more preferably 40 seconds or more and 1,500 seconds or less. The Peck flatness can be obtained in accordance with Japanese Industrial Standards (JIGS) P8119, "Method for Testing Flatness of Paper and Cardboard Using Peck Tester", and TAPIR Standard Method T479.

In the present invention, the Peck flatness for a mat degree of the backing layer is preferably 1,200 seconds or less and 10 seconds or more, more preferably 800 seconds or less and 20 seconds or more, and most preferably 500 seconds or less and 40 seconds or more.

In the present invention, the matting agent is preferably contained in the outermost surface layer of the photosensitive layer or a layer that functions as the outermost surface layer, a layer close to the outer surface, or a layer that functions as the protecting layer.

The pH of the film surface of the thermal-developable photosensitive material before thermal development in the present invention is preferably 7.0 or lower, and more preferably 6.6 or lower. Although the lower limit thereof is not specifically limited, it is about 3. The most preferable pH range is between 4 and 6.2. The control of the pH of the film surface using an organic acid such as phthalic acid derivatives, a non-volatile acid such as sulfuric acid, or a volatile base such as ammonia is preferable from the point of view of lowering the pH of the film surface. In particular, since ammonia is easily evaporated and can be removed before the coating step or thermal development, it is preferable for achieving a low pH of the film surface.

The combined use of a non-volatile base, such as sodium hydroxide, potassium hydroxide, and lithium hydroxide, with ammonia is also preferable.

In the layers of the present invention, such as photosensitive layer, the protecting layer, and the backing layer, a hardener can be used. Examples of hardeners including chrome alum, 2,4-dichloro-6-hydroxy-s-triazine sodium salt, N,N-ethylene bis(vinylsulfone acetamide), and N,N-propylene bis(vinylsulfone acetamide); as well as multivalent metal ions; polyisocyanates; epoxy compounds; and vinylsulfone-based compounds are preferably used.

The hardener is added in the form of a solution, and the time for adding the solution to the coating liquid for the protecting layer is 180 minutes before to immediately before coating, preferably 60 minutes to 10 seconds before coating. The methods and conditions for mixing are not specifically limited as long as the effect of the present invention is sufficiently achieved. Specific methods for mixing include a method of mixing in a tank wherein the average retention time calculated from the flow rate and the quantity to the coater is controlled to a desired time; or a method to use a static mixer.

For a transparent support, polyester, especially polyethylene terephthalate undergone heat treatment within a temperature range between 130° C. and 185° C. is preferably used for relieving internal strain remaining in the film during biaxial drawing, and eliminating thermal shrinkage strain occurring during thermal development. In the case of a thermal-developable photosensitive material, the transparent support may be colored with a blue dye, or may be not colored. It is preferable that the primer techniques of water-soluble polyester, styrene-butadiene copolymer, and vinylidene chloride copolymers are applied to the support.

The thermal-developable photosensitive material is preferably of a monosheet type (a type that can form images on a thermal-developable photosensitive material not using other sheets as in image-receiving materials).

To the thermal-developable photosensitive material, an anti-oxidant, a stabilizer, a plasticizer, a ultraviolet absorber, or coating additives may further be added. The various additives are added to either the photosensitive layer or a non-photosensitive layer.

The thermal-developable photosensitive material in the present invention can be applied using any methods. Specifically, various coating operations can be used, including extrusion coating, slide coating, curtain coating, dip coating, knife coating, flow coating, and extrusion coating using a hopper. Extrusion coating or slide coating are preferably used, and slide coating is most preferably used.

The organic-silver-salt-containing coating liquid in the present invention is preferably a so-called thixotropic fluid. The viscosity at a shear rate of $0.1\ s^{-1}$ of the coating liquid is preferably 400 mPa·s or more and 100,000 mPa·s or less, and more preferably 500 mPa·s or more and 200,000 mPa·s or less. The viscosity at a shear rate of $1000\ s^{-1}$ is preferably 1 mPa·s or more and 200 mPa·s or less, and more preferably 5 mPa·s or more and 80 mPa·s or less.

The thermal-developable photosensitive material of the present invention may be developed using any methods, and normally, it is developed by heating the thermal-developable photosensitive material exposed image-wise. The developing temperature is preferably 80° C. to 250° C., and more preferably 100° C. to 140° C. The developing time is preferably 1 second to 60 seconds, more preferably 5 seconds to 30 seconds, and most preferably 10 seconds to 20 seconds.

The preferable system for thermal development is a plate-heater system. The preferable thermal development system by a plate-heater system is a thermal development system for obtaining visible images by contacting a thermal-developable photosensitive material wherein a latent image has been formed with a heating means in the thermal development section. The thermal development system is characterized in that the heating means comprises a plate heater, a plurality of presser rollers are disposed facing and along a surface of the plate heater, and the thermal-developable photosensitive material is passed between the presser rollers and the plate heater to perform thermal development. It is preferable that the plate heater is divided into two to six stages, and that the temperature of the end portion is lowered by 1 to 10° C. Such a method can exclude moisture or organic solvents contained in the thermal-developable photosensitive material out of the system, and the deformation of the support of the thermal-developable photosensitive material suddenly heated can be prevented.

Although the photosensitive material of the present invention can be exposed using any methods, a preferable light source for exposure is laser beams. The preferable laser beams for the present invention include gas laser ($Ar^+$, He—Ne), YAG laser, dye laser, and semiconductor laser. A semiconductor laser and a second higher-harmonic-generating element can also be used. Red to infrared emitting gas or a semiconductor laser is preferable.

Laser imagers for medical use having an exposure section and a thermal development section include Fuji Medical Dry Laser Imager FM-DP L. The FM-DP L is described in Fuji Medical Review No. 8, pages 39 to 55, and these techniques can be applied to the laser imager of the thermal-developable photosensitive material of the present invention. These techniques can also be applied to the thermal-developable photosensitive material for the laser imager in "AD network" proposed by Fuji Medical System as a network system meeting the DICOM Standards.

The thermal-developable photosensitive material of the present invention forms black-and-white images by silver images, and is preferably used in the thermal-developable photosensitive material for medical diagnostics, the thermal-developable photosensitive material for industrial photography, the thermal-developable photosensitive material for printing, and the thermal-developable photosensitive material for COM.

(Fabrication of PET Support)

Using terephthalic acid and ethylene glycol, PET having an intrinsic viscosity (IV) of 0.66 (measured in a mixed solvent of phenol and tetrachloroethane (6:4 by mass) at 25° C.) was obtained according to a normal method. This was palletized, dried at 130° C. for 4 hours, melted at 300° C., extruded through a T-die, and quenched to form a non-oriented film of a thickness after heat fixing of 175 μm.

This film was longitudinally stretched 3.3 times using rolls of different circumferential speed, and transversally stretched 4.5 times using a tenter. The temperatures for stretching were 110° C. and 130° C., respectively. Thereafter, the film was heat-fixed at 240° C. for 20 seconds, and relaxed by 4% in the transverse direction at the same temperature. Then, the portion of the film held by the chuck of the tenter was cut off, the both edges were knurled, the film was wound at 4 kg/cm² to obtain a roll of the film having a thickness of 175 μm.

(Corona Treatment of Surface)

The both surfaces of the support were treated using a 6-kVA solid-state corona treatment system of Piller Inc. at room temperature at 20 mn/min. From the readings of current and voltage, it was known that the support was treated at 0.375 kV·A·min/m². The treatment frequency was 9.6 kHz, and the gap clearance between the electrode and the dielectric roller was 1.6 mm.

(Fabrication of primer coating support)
(1) Preparation of primer coating liquid

| Formulation (for primer-coating layer in the photosensitive layer side) | |
|---|---|
| Pesresin A-515GB (30% by mass solution) (Takamatsu Oil & Fat) | 234 g |
| Polyethylene glycol monononyl phenyl ether (average ethylene oxide number = 8.5) (10% by mass solution) | 21.5 g |
| MP-1000 (Soken Chemical & Engineering) (polymer fine particles, average particle diameter: 0.4 μm) | 0.91 g |
| Distilled water | 744 mL |
| Formulation (for first layer in back surface) | |
| Styrene-butadiene copolymer latex (solid content: 40% by mass, styrene/butadiene mass ratio: 68/32) | 158 g |
| 2,4-dichloro-6-hydroxy-S-triazine, sodium salt (8% by mass aqueous solution) | 20 g |
| Sodium laurylbenzenesulfonate (1% by mass aqueous solution) | 10 mL |
| Distilled water | 854 mL |
| Formulation (for second layer in back surface) | |
| $SnO_2/SbO$ (9/1 mass ratio, average particle diameter: 0.038 μm, 17 mass % dispersion) | 84 g |
| Gelatin (10% by mass aqueous solution) | 89.2 g |
| Metolose TC-5 (2% by mass aqueous solution) (Shin-Etsu Chemical) | 8.6 g |
| MP-1000 (Soken Chemical & Engineering) | 0.01 g |

(Fabrication of primer coating support)
(1) Preparation of primer coating liquid

| | |
|---|---|
| Sodium dodecylbenzene sulfonate (1% by mass aqueous solution) | 10 mL |
| NaOH (1% by mass) | 6 mL |
| Prokicell (ICI) | 1 mL |
| Distilled water | 805 mL |

(Fabrication of Primer Coated Support)

After the both surfaces of the above-described biaxially oriented polyethylene terephthalate support having a thickness of 175 μm was subjected to the above-described corona discharge treatment, one surface (photosensitive layer side) was coated with the primer coating liquid of the above-described formulation with a wire bar so that the wet coating quantity became 6.6 mL/m$^2$ (per surface), and dried at 180° C. for 5 minutes. Then, the other surface (back face) was coated with the primer coating liquid of above-described formulation with a wire bar so that the wet coating quantity became 5.7 mL/m$^2$, and dried at 180° C. for 5 minutes. Furthermore, the other surface (back face) was coated with the primer coating liquid of above-described formulation with a wire bar so that the wet coating quantity became 7.7 mL/m$^2$, and dried at 180° C. for 6 minutes to fabricate a primer coated support.

(Preparation of Back-face Coating Liquid)
(Preparation of Fine Solid Particle Dispersion (a) of Basic Precursor)

With 220 mL of distilled water, 64 g of the basic precursor compound 11, 28 g of diphenyl sulfide, and 10 g of Demol N (surfactant, Kao Corp.) were mixed, and the mixture was subjected to bead dispersion using a sand mill (¼-gallon sand grinder mill, Aimex) to form a fine solid particle dispersion (a) of the basic precursor having an average particle diameter of 0.2 μm.

(Preparation of Fine Solid Particle Dispersion of Dye)

With 305 mL of distilled water, 9.6 g of cyanine dye compound 13 and 5.8 g of sodium p-dodecylbenzenesulfonate were mixed, and the mixture was subjected to bead dispersion using a sand mill (¼-gallon sand grinder mill, Aimex) to form a fine solid particle dispersion of the dye having an average particle diameter of 0.2 μm.

(Preparation of Anti-halation Coating Liquid)

Seventeen grams of gelatin, 9.6 g of polyacrylamide, 70 g of the above-described fine solid particle dispersion (a) of the basic precursor, 56 g of the above-described fine solid particle dispersion of the dye, 1.5 g of fine particles of monodisperse polymethyl methacrylate (average particle size: 8 μm, standard deviation of particle diameters: 0.4), 0.03 g of benzoisothiazolinone, 2.2 g of sodium polyethylenesulfonate, 0.2 g of blue dye compound 14, 3.9 g of yellow dye compound 15, and 844 mL of water were mixed to prepare an anti-halation coating.

(Preparation of Back Face Protecting Coating)

A container was maintained at a temperature of 40° C., 50 g of gelatin, 0.2 g of sodium polystyrenesulfonate, 2.4 g of N,N-ethylenebis(vinylsulfonacetamide), 1 g of sodium t-octylphenoxyethoxyethanesulfonate, 30 mg of benzoisothizolinone, 37 mg of a fluorine-based surfactant (F-1: N-perfluorooctylsulfonyl-N-propylalanine, potassium salt), 0.15 g of a fluorine-based surfactant (F-2: polyethylene glycol mono (N-perfluorooctylsulfonyl-N-propyl-2-aminoethyl) ether (average polymerization degree of ethylene oxide: 15)), 64 mg of a fluorine-based surfactant (F-3), 32 mg of a fluorine-based surfactant (F-4), 8.8 g of acrylic acid/ethyl acrylate copolymer (copolymerization mass ratio: 5/95), 0.6 g of Aerosol OT (American Cyanamide), 1.8 g of liquid paraffin emulsion (as liquid paraffin), and 950 mL of water were mixed to prepare a back face protecting coating liquid.

<Preparation of Silver Halide Emulsion>

A liquid prepared by adding 3.1 mL of 1% by mass solution of potassium bromide, 3.5 mL of sulfuric acid of a 0.5 mole/L concentration, and 31.7 g of phthalated gelatin to 1421 mL of distilled water was maintained at a temperature of 30° C. while stirring in a stainless-steel reaction vessel, solution A of 22.22 g of silver nitrate in distilled water diluted to 95.4 mL, and solution B of 15.3 g of potassium bromide and 0.8 g of potassium iodide in distilled water diluted to a volume of 97.4 mL were totally added at a constant flow rate in 45 seconds. Thereafter, 10 mL of 3.5% by mass aqueous solution of hydrogen peroxide was added, and 10.8 mL of 10% by mass aqueous solution of benzimidazol was further added. Furthermore, solution C of 51.86 g of silver nitrate in distilled water diluted to 317.5 mL was totally added at a constant flow rate in 20 minutes; and solution D of 2.2 g of potassium iodide in distilled water diluted to a volume of 400 mL was added by the controlled double-jet method maintaining pAg at 8.1. Hexachloroiridic (III) acid, potassium salt was totally added in a quantity ratio of $1 \times 10^{-4}$ mole to 1 mole of silver 10 minutes after starting the addition of solutions C and D. Also, an aqueous solution of potassium hexacyanoferrate (III) was added in a quantity ratio of $3 \times 10^{-4}$ mole to 1 mole of silver 5 seconds after completing the addition of solution C. Using sulfuric acid of a 0.5 mole/L concentration, pH was adjusted to 3.8, stirring was stopped, and settling, desalination, and water washing were performed. Using sodium hydroxide of a 1 mole/L concentration, pH was adjusted to 5.9, to form a silver halide dispersion of pAg of 8.0.

The above-described silver halide dispersion was maintained at a temperature of 38° C. while stirring, 5 mL of 0.34% by mass solution of 1,2-benzoisothiazoline-3-one in methanol was added, then 40 minutes later, a methanol solution of spectrally sensitizing dye A and sensitizing dye B in a mole ratio of 1:1 was added in a quantity of $1.2 \times 10^{-3}$ mole as the total quantity of the sensitizing dyes A and B, and 1 minute later, the temperature was elevated to 47° C. Twenty minutes after the elevation of the temperature, a methanol solution of sodium benzenethio sulfonate was added in a quantity of $7.6 \times 10^{-5}$ mole to 1 mole of silver, and 5 minutes later, the tellurium sensitizing dye B in a quantity of $2.9 \times 10^{-4}$ mole to 1 mole of silver was added, and the dispersion was aged for 91 minutes. To the dispersion, 1.3 mL of 0.8% by mass solution of N,N'-dihydroxy-N"-diethylmelamine in methanol was added, and 4 minutes later, a methanol solution of 5-methyl-2-mercaptobenzimidazole was added in a quantity of $4.8 \times 10^{-3}$ mole to 1 mole of silver and a methanol solution of 1-phenyl-2-hyptyl-5-mercapto-1,3,4-triazole was added in a quantity of $5.4 \times 10^{-3}$ mole to 1 mole of silver, to form silver halide emulsion 1.

The particles in the prepared silver halide emulsion were silver iodide bromide particles evenly containing 3.5 mol % of iodine of an average sphere-equivalent diameter of 0.042 μm and a coefficient of variation of the sphere-equivalent diameter of 20%. The particle size and the like were obtained from the average of 1000 particles using an electron microscope. The ratio of the {100} face of these particles was calculated to be 80% using the Kubelka-Munch method.

<Preparation of Silver Halide Emulsion 2>

Silver halide emulsion 2 was prepared in the same manner as in the preparation of silver halide emulsion 1, except that the liquid temperature in forming particles was changed from 30° C. to 47° C., solution B was changed to 15.9 g of potassium bromide dissolved in distilled water and diluted to 97.4 mL, solution D was changed to 45.8 g of potassium bromide dissolved in distilled water and diluted to 400 mL, time for adding solution C was 30 minutes, and potassium hexacyanoferrate (III) was excluded. In the same manner as in silver halide emulsion 1, precipitation, desalination, water washing, and dispersion were carried out. Furthermore, spectral sensitization and chemical sensitization, and the addition of 5-methyl-2-mercaptobenzimidazole and 1-phenyl-2-heptyl-5-mercapto-1,3,4-triazole were carried out in the same manner as in the preparation of silver halide emulsion 1, except that the quantity of the methanol solution of spectrally sensitizing dye A and sensitizing dye B in a mole ratio of 1:1 was changed to $7.5 \times 10^{-4}$ mole as the total quantity of the sensitizing dyes A and B, the quantity of the tellurium sensitizing dye B to $1.1 \times 10^{-4}$ mole to 1 mole of silver, and the quantity of 1-phenyl-2-hyptyl-5-mercapto-1,3,4-triazole was changed to $3.3 \times 10^{-3}$ mole to 1 mole of silver, to form silver halide emulsion 2. The emulsion particles in silver halide emulsion 2 were pure silver bromide cubic particles of an average sphere-equivalent diameter of 0.008 μm and a coefficient of variation of the sphere-equivalent diameter of 20%.

<Preparation of Silver Halide Emulsion 3>

Silver halide emulsion 3 was prepared in the same manner as in the preparation of silver halide emulsion 1, except that the liquid temperature in forming particles was changed from 30° C. to 27° C. Also, in the same manner as in silver halide emulsion 1, precipitation, desalination, water washing, and dispersion were carried out. In the same manner as in the preparation of silver halide emulsion 1, except that the spectrally sensitizing dye A and spectrally sensitizing dye B in a mole ratio of 1:1 was changed to a solid dispersion (aqueous solution of gelatin) and the quantity was changed to $6 \times 10^{-3}$ mole as the total quantity of the sensitizing dyes A and B, and the quantity of the tellurium sensitizing dye B to $5.2 \times 10^{-4}$ mole to 1 mole of silver, to form silver halide emulsion 3. The emulsion particles in the silver halide emulsion 3 were silver iodide bromide particles containing 3.5 mol % of iodine of an average sphere-equivalent diameter of 0.034 μm and a coefficient of variation of the sphere-equivalent diameter of 20%.

<Preparation of Mixed Emulsion A for Coating Liquid>

Seventy percent by mass of the silver halide emulsion 1, 15% by mass of the silver halide emulsion 2, and 15% by mass of the silver halide emulsion 3 were dissolved, and $7 \times 10^{-3}$ mole of benzothiazolium iodide for 1 mole of silver was added in a 1% by mass aqueous solution. Furthermore, water was added so that the content of silver halide in 1 kg of the mixed emulsion for coating liquid became 38.2 g as silver.

<Preparation of Silver Fatty-acid Salt Dispersion>

A sodium behenate solution was obtained by mixing 87.6 kg of behenic acid (Henkel, tradename: Edenor C22-85R), 423 L of distilled water, 49.2 L of a 5 mole/L aqueous solution of NaOH, and 120 L of tert-butanol, and stirring at 75° C. for 1 hour to allow to react. Separately, 206.2 L of an aqueous solution containing 40.4 Kg of silver nitrate (pH 4.0) was prepared, and maintained at a temperature of 10° C. A reaction vessel containing 635 L of distilled water and 30 L of tert-butanol was maintained at a temperature of 30° C., and the total quantity of the above-described sodium behenate solution and the total quantity of the aqueous solution of silver nitrate were added stirring well in 93 minutes 15 seconds and 90 minutes, respectively. In this time, only the aqueous solution of silver nitrate was added for 11 minutes from the start of adding, then, the addition of the sodium behenate solution was started, and only the sodium behenate solution was for 14 minutes 15 seconds after the completion of adding the aqueous solution of silver nitrate. The temperature in the reaction vessel at this time was 30° C., and the ambient temperature was controlled so that the liquid temperature is maintained constant. The piping for adding the sodium behenate solution was warmed by circulating warm water in the outer pipe of the double-pipe system, and the liquid temperature at the outlet of the adding nozzle was controlled to be 75° C. The piping for adding the aqueous solution of silver nitrate was warmed by circulating cold water in the outer pipe of the double-pipe system. The location of adding the sodium behenate solution and the location of the aqueous solution of silver nitrate were symmetrical about the axis of stirring, and adjusted to the height so as not to contact the reaction liquid.

After completing the addition of the sodium behenate solution, the temperature of the solution was maintained at the same temperature stirring for 20 minutes, and elevated to 35° C. in 30 minutes, and the solution was aged for 210 minutes. Immediately after the completion of aging, pure water was added in the tank to stop aging, the solution was transferred from the feeding kettle by head pressure or using a pump, the solid matter was filtered by centrifugal filtration, and washed with water until the conductivity of the filtrate becomes 30 μS/cm. Thus, the fatty salt of silver was obtained. The obtained solid matter was stored as wet cake (solid content: 45% by mass) without drying.

The form of the obtained silver behenate particles observed by electron microscopic photography was flake crystals having average values of a=0.14 μm, b=0.4 μm, c=0.6 μm; an average aspect ratio of 5.2; an sphere-equivalent diameter of 0.52 μm and a coefficient of variation of the sphere-equivalent diameter of 15%. (a, b, and c are defined herein.)

To the wet cake equivalent to 260 kg of the dry solid, 19.3 kg of polyvinyl alcohol (trade name: PVA-217) and water were added to make the total quantity of 1000 kg, the mixture was made to be slurry using a dissolver blade, and preliminarily dispersed with a pipe-line mixer (MIZUHO, PM-10).

Next, the preliminarily dispersed stock slurry was treated 3 times with a dispersing machine (trade name: Micro Fluidizer M-610, Microfluidex International Corporation, using a Z-type interaction chamber) of which pressure was adjusted to 1260 kg/cm$^2$, to form silver behenate dispersion. The dispersion temperature of 18° C. was maintained by furnishing coiled heat exchangers before and after the interaction chamber, respectively, and controlling the temperature of the coolant.

<Preparation of Reducer-1 Dispersion>

To 10 kg of the reducer-1 (1,1-bis(2-hydroxy-3.5-dimethylphenyl)-3,5,5-trimethylhexane) and 10 kg of a 20% by mass aqueous solution of modified polyvinyl alcohol (KURARAY, POVAL MP203), 16 kg of water was mixed, and the mixture was stirred well to form a slurry. The slurry was pumped with a diaphragm pump to a horizontal sand mill packed with zirconia beads of an average diameter of 0.5 mm (IMEX, UVM-2), whereby it was dispersed for 3 hours 30 minutes, then, 0.2 g of benzoisothiazolinone sodium salt and water were added to adjust so that the concentration of the reducer became 25% by mass to form a reducer-1 dispersion. The reducer particles in thus obtained reducer dispersion had a median diameter of 0.42 μm and a maximum particle diameter of 2.0 μm or smaller. The obtained reducer dispersion was filtered with a polypropylene filter of a pore diameter of 10.0 μm to remove foreign matter, such as dust, and stored.

<Preparation of Reducer-2 Dispersion>

To 10 kg of the reducer-2 (2,2'-isobutylidene-bis-(4,6-dimethylphenol)) and 10 kg of a 20% by mass aqueous solution of modified polyvinyl alcohol (KURARAY, POVAL MP203), 16 kg of water was mixed, and the mixture was stirred well to form a slurry. The slurry was pumped with a diaphragm pump to a horizontal sand mill packed with zirconia beads of an average diameter of 0.5 mm (IMEX, UVM-2), whereby it was dispersed for 3 hours 30 minutes, then, 0.2 g of benzoisothiazolinone sodium salt and water were added to adjust so that the concentration of the reducer became 25% by mass to form a reducer-2 dispersion. The reducer particles in thus obtained reducer dispersion had a median diameter of 0.38 μm and a maximum particle diameter of 2.0 μm or smaller. The obtained reducer dispersion was filtered with a polypropylene filter of a pore diameter of 10.0 μm to remove foreign matter, such as dust, and stored.

<Preparation of Reducer Complex-3 Dispersion>

To 10 kg of the reducer complex-3 (1:1 complex of 2,2'-methylene-bis(4-ethyl-6-tert-butylphenol) and hydrogen linkable compound-1 (triphenylphosphine oxide)), 0.12 kg of triphenylphosphine oxide, and 16 kg of a 10% by mass aqueous solution of modified polyvinyl alcohol (KURARAY, POVAL MP203), 7.2 kg of water was mixed, and the mixture was stirred well to form a slurry. The slurry was pumped with a diaphragm pump to a horizontal sand mill packed with zirconia beads of an average diameter of 0.5 mm (IMEX, UVM-2), whereby it was dispersed for 4 hours 30 minutes, then, 0.2 g of benzoisothiazolinone sodium salt and water were added to adjust so that the concentration of the reducer became 25% by mass to form a reducer complex-3 dispersion. The reducer particles in thus obtained reducer dispersion had a median diameter of 0.46 μm and a maximum particle diameter of 1.6 μm or smaller. The obtained reducer dispersion was filtered with a polypropylene filter of a pore diameter of 3.0 μm to remove foreign matter, such as dust, and stored.

<Preparation of Reducer-4 Dispersion>

To 10 kg of the reducer-4 (2,2'-methylene-bis(4-ethyl-6-tert-butylphenol)) and 20 kg of a 10% by mass aqueous solution of modified polyvinyl alcohol (KURARAY, POVAL MP203), 6 kg of water was mixed, and the mixture was stirred well to form a slurry. The slurry was pumped with a diaphragm pump to a horizontal sand mill packed with zirconia beads of an average diameter of 0.5 mm (IMEX, UVM-2), whereby it was dispersed for 3 hours 30 minutes, then, 0.2 g of benzoisothiazolinone sodium salt and water were added to adjust so that the concentration of the reducer became 25% by mass to form a reducer-4 dispersion. The reducer particles in thus obtained reducer dispersion had a median diameter of 0.40 μm and a maximum particle diameter of 1.5 μm or smaller. The obtained reducer dispersion was filtered with a polypropylene filter of a pore diameter of 3.0 μm to remove foreign matter, such as dust, and stored.

<Preparation of Reducer-5 Dispersion>

To 10 kg of the reducer-5 (2,2'-methylene-bis(4-methyl-6-tert-butylphenol)) and 20 kg of a 10% by mass aqueous solution of modified polyvinyl alcohol (KURARAY, POVAL MP203), 6 kg of water was mixed, and the mixture was stirred well to form a slurry. The slurry was pumped with a diaphragm pump to a horizontal sand mill packed with zirconia beads of an average diameter of 0.5 mm (IMEX, UVM-2), whereby it was dispersed for 3 hours 30 minutes, then, 0.2 g of benzoisothiazolinone sodium salt and water were added to adjust so that the concentration of the reducer became 25% by mass to form a reducer-5 dispersion. The reducer particles in thus obtained reducer dispersion had a median diameter of 0.38 μm and a maximum particle diameter of 1.5 μm or smaller. The obtained reducer dispersion was filtered with a polypropylene filter of a pore diameter of 3.0 μm to remove foreign matter, such as dust, and stored.

<Preparation of Hydrogen Linkable Compound-2 Dispersion>

To 10 kg of the hydrogen linkable compound-2 (tri(4-t-butylphenyl)phosphine oxide) and 20 kg of a 10% by mass aqueous solution of modified polyvinyl alcohol (KURARAY, POVAL MP203), 10 kg of water was mixed, and the mixture was stirred well to form a slurry. The slurry was pumped with a diaphragm pump to a horizontal sand mill packed with zirconia beads of an average diameter of 0.5 mm (INEX, UVM-2), whereby it was dispersed for 3 hours 30 minutes, then, 0.2 g of benzoisothiazolinone sodium salt and water were added to adjust so that the concentration of the reducer became 22% by mass to form a hydrogen linkable compound-2 dispersion. The reducer particles in thus obtained reducer dispersion had a median diameter of 0.35 μm and a maximum particle diameter of 1.5 μm or smaller. The obtained reducer dispersion was filtered with a polypropylene filter of a pore diameter of 3.0 μm to remove foreign matter, such as dust, and stored.

<Preparation of Organic Polyhalogen Compound-1 Dispersion>

To 10 kg of the organic polyhalogen compound-1 (2-tribromomethane sulfonyl naphthalene), 10 kg of a 20% by mass aqueous solution of modified polyvinyl alcohol (KURARAY, POVAL MP203), and 0.4 kg of a 20% by mass aqueous solution of sodium triisopropylnaphthalenesulfonate, 16 kg of water was mixed, and the mixture was stirred well to form a slurry. The slurry was pumped with a diaphragm pump to a horizontal sand mill packed with zirconia beads of an average diameter of 0.5 mm (IMEX, UVM-2), whereby it was dispersed for 5 hours, then, 0.2 g of benzoisothiazolinone sodium salt and water were added to adjust so that the concentration of the organic polyhalogen compound became 23.5% by mass to form an organic polyhalogen compound-1 dispersion. The organic polyhalogen compound particles in thus obtained organic polyhalogen compound dispersion had a median diameter of 0.36 μm and a maximum particle diameter of 2.0 μm or smaller. The obtained organic polyhalogen compound dispersion was filtered with a polypropylene filter of a pore diameter of 10.0 μm to remove foreign matter, such as dust, and stored.

<Preparation of Organic Polyhalogen Compound-2 Dispersion>

To 10 kg of the organic polyhalogen compound-2 (tribromomethane sulfonyl benzene), 10 kg of a 20% by mass aqueous solution of modified polyvinyl alcohol (KURARAY, POVAL MP203), and 0.4 kg of a 20% by mass aqueous solution of sodium triisopropylnaphthalenesulfonate, 14 kg of water was mixed, and the mixture was stirred well to form a slurry. The slurry was pumped with a diaphragm pump to a horizontal sand mill packed with zirconia beads of an average diameter of 0.5 mm (IMEX, UVM-2), whereby it was dispersed for 5 hours, then, 0.2 g of benzoisothiazolinone sodium salt and water were added to adjust so that the concentration of the organic polyhalogen compound became 26% by mass to form an organic polyhalogen compound-2 dispersion. The organic polyhalogen compound particles in thus obtained organic polyhalogen compound dispersion had a median diameter of 0.41 μm and a maximum particle diameter of 2.0 μm or smaller. The obtained organic polyhalogen compound dispersion was filtered with a polypropylene filter of a pore diameter of 10.0 μm to remove foreign matter, such as dust, and stored.

<Preparation of Organic Polyhalogen Compound-3 Dispersion>

To 10 kg of the organic polyhalogen compound-3 (N-butyl-3-tribromomethanesulfonyl benzamide), 10 kg of a 20% by mass aqueous solution of modified polyvinyl alcohol (KURARAY, POVAL MP203), and 0.4 kg of a 20% by mass aqueous solution of sodium triisopropylnaphthalenesulfonate, 8 kg of water was mixed, and the mixture was stirred well to form a slurry. The slurry was pumped with a diaphragm pump to a horizontal sand mill packed with zirconia beads of an average diameter of 0.5 mm (IMEX, UVM-2), whereby it was dispersed for 5 hours, then, 0.2 g of benzoisothiazolinone sodium salt and water were added to adjust so that the concentration of the organic polyhalogen compound becomes 25% by mass to form an organic polyhalogen compound-3 dispersion. The organic polyhalogen compound particles in thus obtained organic polyhalogen compound dispersion had a median diameter of 0.36 μm and a maximum particle diameter of 1.5 μm or smaller. The obtained organic polyhalogen compound dispersion was filtered with a polypropylene filter of a pore diameter of 3.0 μm to remove foreign matter, such as dust, and stored.

<Preparation of Phthalazine Compound-1 Solution>

Eight kilograms of modified polyvinyl alcohol MP203 (KURARAY) was dissolved in 174.57 kg of water, then 3.15 kg of a 20% by mass aqueous solution of sodium triisopropylnaphthalenesulfonate and 14.28 kg of a 70% by mass aqueous solution of phthalazine compound-1 (6-isopropylphthalazine) were added to prepare 5% by mass solution of phthalazine compound-1.

<Preparation of Mercapto Compound-1 Solution>

Seven grams of mercapto compound-1 (1-(3-sulfophenyl)-5-mercapto tetrazole sodium salt) was dissolved in 993 g of water to prepare 0.7% by mass aqueous solution of mercapto compound-1.

<Preparation of Pigment-1 Dispersion>

To 64 g of C. I. Pigment Blue 60 and 6.4 g of Kao DEMOL N, 250 g of water was added, and the mixture was stirred well to form slurry. Together the slurry, 800 g of zirconia beads of an average diameter of 0.5 mm were fed in a vessel, and dispersed for 25 hours with a dispersing machine (¼ G Sand Grinder Mill, IMEX) to form a pigment-1 dispersion. The pigment particles in thus obtained pigment dispersion had an average particle diameter of 0.21 μm.

<Preparation of SBR Latex Emulsion>

SBR latex of a Tg of 23° C. was prepared as follows: Using ammonium persulfate as a polymerization initiator, and an anionic surfactant as an emulsifier, 70.5 parts by mass of styrene, 26.5 parts by mass of butadiene, and 3 parts by mass of acrylic acid were undergone emulsion polymerization, and aged at 80° C. for 8 hours. Thereafter, the emulsion was cooled to 40° C.; the pH was adjusted to 7.0 using ammonia water; and Sandet BL (Sanyo Chemical Industries) was added to a concentration of 0.22%. Next, a 5% aqueous solution of sodium hydroxide was added to pH 8.3, and furthermore, the pH was adjusted to 8.4 using ammonia water. The mole ratio of $Na^+$ ions and $NH_4^+$ ions used in this time was 1:2.3. Furthermore, 0.15 mL of a 7% aqueous solution of benzoisothiazolinone sodium salt was added to 1 kg of the emulsion to prepare an SBR latex emulsion.

(SBR latex: St (70.5)-Bu (26.5)-AA (3)-latex) Tg: 23° C.

Average particle diameter: 0.1 μm; concentration: 43% by mass; equilibrium water content at 25° C., 60% RH: 0.6% by mass; ionic conductivity: 4.2 mS/cm (measured using DKK-TOA conductivity meter CM-30S for the latex stock emulsion (43% by mass) at 25° C.); pH: 8.4

SBR latex of different Tg was prepared by the same manner except for changing the contents of styrene and butadiene.

<Preparation of Emulsion Layer (Photosensitive Layer) Coating Liquid-1>

The emulsion layer coating liquid prepared by sequentially adding 1000 g of the dispersion of fatty-acid salt of silver obtained as described above, 125 mL of water, 113 g of the dispersion of the reducer-1, 91 g of the dispersion of the reducer-2, 27 g of the dispersion of the pigment-1, 82 g of the dispersion of the organic polyhalogen compound-1, 40 g of the dispersion of the organic polyhalogen compound-2, 173 g of the solution of the phthalazine compound-1, 1082 g of the SBR latex (Tg: 20.5° C.) emulsion, and 9 g of the aqueous solution of the mercapto compound-1, adding 158 g of the silver halide mixed emulsion A immediately before coating, and mixing well was transferred as it is to a coating die and applied.

The viscosity of the emulsion layer coating liquid measured at 40° C. using a B-viscometer (Tokyo Keiki) was 85 mPa·s (No. 1 rotor, 60 rpm).

The viscosities of the coating liquid at 25° C. measured using an RFS Fluid Spectrometer manufactured by Rheometrix Far East at shear rates of 0.1 $s^{-1}$, 1 $s^{-1}$, 10 $s^{-1}$, 100 $s^{-1}$, and 1000 $s^{-1}$ were 1500 mPa·s, 220 mPa·s, 70 mPa·s, 40 mPa·s, and 20 mPa·s, respectively.

<Preparation of Emulsion Layer (Photosensitive Layer) Coating Liquid-2>

The emulsion layer coating liquid prepared by sequentially adding 1000 g of the dispersion of fatty-acid salt of silver obtained as described above, 104 mL of water, 30 g of the dispersion of the pigment-1, 21 g of the dispersion of the organic polyhalogen compound-2, 69 g of the dispersion of the organic polyhalogen compound-3, 173 g of the solution of the phthalazine compound-1, 1082 g of the SBR latex (Tg: 23° C.) emulsion, 258 g of the dispersion of the reducer complex-3, and 9 g of the solution of the mercapto compound-1, adding 110 g of the silver halide mixed emulsion A immediately before coating, and mixing well was transferred as it is to a coating die and applied.

<Preparation of Emulsion Layer (Photosensitive Layer) Coating Liquid-3>

The emulsion layer coating liquid prepared by sequentially adding 1000 g of the dispersion of fatty-acid salt of silver obtained as described above, 95 mL of water, 73 g of the dispersion of the reducer-4, 68 g of the dispersion of the reducer-5, 30 g of the dispersion of the pigment-1, 21 g of the dispersion of the organic polyhalogen compound-2, 69 g of the dispersion of the organic polyhalogen compound-3, 173 g of the solution of the phthalazine compound-1, 1082 g of the core-shell type SBR latex (core Tg: 20° C./shell Tg: 30° C.=70/30) emulsion, 124 g of the dispersion of the hydrogen-linkable compound-2, and 9 g of the aqueous solution of the mercapto compound-1, adding 110 g of the silver halide mixed emulsion A immediately before coating, and mixing well was transferred as it is to a coating die and applied.

<Preparation of Intermediate Emulsion Layer Coating Liquid>

The intermediate emulsion layer coating liquid prepared by mixing 772 g of a 10% by mass aqueous solution of polyvinyl alcohol PVA-205 (KURARAY), 5.3 g of the dispersion of pigment, 226 g of a 27.5% by mass emulsion of a methyl methacrylate/styrene/butyl acrylate/hydroxyethyl methacrylate/acrylic acid copolymer (copolymerization ratio by mass: 64/9/20/5/2) latex, 2 mL of a 5% by mass aqueous solution of Aerosol OT (American Cyanamide), 10.5 mL of a 20% by mass aqueous solution of diammonium phthalate, and adding water to make the total quantity 880 g, adjusting the pH to 7.5 with NaOH was transferred to a coating die so as to be 10 mL/m$^2$.

The viscosity of the coating liquid measured at 40° C. using a B-viscometer was 21 mPa·s (No. 1 rotor, 60 rpm).

<Preparation of First Emulsion Protecting Layer Coating Liquid>

The coating liquid prepared by dissolving 64 g of inert gelatin in water, adding 80 g of a 27.5% by mass emulsion of a methyl methacrylate/styrene/butyl acrylate/hydroxyethyl methacrylate/acrylic acid copolymer (copolymerization ratio by mass: 64/9/20/5/2) latex, 23 mL of a 10% by mass methanol solution of phthalic acid, 23 mL of a 10% by mass aqueous solution of 4-methlyphthalic acid, 28 mL of sulfuric acid of a concentration of 0.5 mole/L, 5 mL of a 5% by mass aqueous solution of Aerosol OT (American Cyanamide), 0.5 g of phenoxy ethanol, and 0.1 g of benzoisothiazolinone, adding water to make the total quantity 750 g, and mixing 26 mL of a 4% by mass solution of chrome alum with a static mixer immediately before coating was transferred to a coating die so as to be 18.6 mL/m$^2$.

The viscosity of the coating liquid measured at 40° C. using a B-viscometer was 17 mPa·s (No. 1 rotor, 60 rpm).

<Preparation of Second Emulsion Protecting Layer Coating Liquid>

The coating liquid for surface-protecting layer prepared by dissolving 80 g of inert gelatin in water, adding 102 g of a 27.5% by mass emulsion of a methyl methacrylate/styrene/butyl acrylate/hydroxyethyl methacrylate/acrylic acid copolymer (copolymerization ratio by mass: 64/9/20/5/2) latex, 3.2 mL of a 5% by mass solution of a fluorine-based surfactant (F-1: N-perfluorooctylsulfonyl-N-propylglycine potassium salt), 32 mL of a 2% by mass aqueous solution of a fluorine-based surfactant (F-2: polyethyleneglycol mono (N-perfluorooctylsulfonyl-N-propyl-2-aminoethyl)ether (average degree of polymerization of ethylene oxide=15), 23 mL of a 5% by mass solution of Aerosol OT (American Cyanamide), 4 g of fine particles of polymethyl methacrylate (average particle diameter: 0.7 μm), 21 g of fine particles of polymethyl methacrylate (average particle diameter: 4.5 μm), 1.6 g of 4-methyl phthalic acid, 4.8 g of phthalic acid, 44 mL of sulfuric acid of a concentration of 0.5 mole/L, and 10 mg of benzoisothiazolinone, adding water to make the total quantity 650 g, and mixing 445 mL of an aqueous solution containing 4% by mass chrome alum and 0.67% by mass phthalic acid with a static mixer immediately before coating was transferred to a coating die so as to be 8.3 mL/m$^2$.

The viscosity of the coating liquid measured at 40° C. using a B-viscometer was 9 mPa·s (No. 1 rotor, 60 rpm).

<Preparation of Thermal-developable Photosensitive Material-1>

The back-face side of the above-described primer support was coated with the anti-halation layer coating liquid so that the coating quantity of the solid matter of the fine solid particle dye became 0.04 g/m$^2$, and was simultaneously coated with the back-face protecting layer coating liquid so that the gelatin quantity became 1.7 g/m$^2$, dried to form a back layer. The surface opposite to the back face, from the primer surface, was simultaneously coated with the emulsion layer, the intermediate layer, the first protecting layer, and the second protecting layer in this order in slide-bead application method to form the sample of the thermal-developable photosensitive material. In this time, the temperatures of the emulsion layer and the intermediate layer, the first protecting layer, and the second protecting layer were adjusted to 31° C., 36° C., and 37° C., respectively.

The coating quantity (g/m$^2$) of each compound as the emulsion layer is as follows:

| | |
|---|---|
| Silver behenate | 6.19 |
| Reducer-1 | 0.67 |
| Reducer-2 | 0.54 |
| Pigment (C. I. Pigment Blue 60) | 0.032 |
| Polyhalogen compound-1 | 0.46 |
| Polyhalogen compound-2 | 0.25 |
| Phthalazine compound-1 | 0.21 |
| SBR latex | 11.1 |
| Mercapto compound-1 | 0.002 |
| Silver halide (as Ag) | 0.145 |

Coating and drying conditions were as follows:

Coating was performed at a speed of 160 m/min, a distance between the end of the coating die and the support of 0.10 mm and 0.30 mm, and the pressure of the reduced-pressure chamber was set 196 Pa to 882 Pa lower than atmospheric pressure. The support was ionized with ion wind before coating.

In the following chilling-zone, the coating liquid was cooled with the air of a dry-bulb temperature between 10° C. and 20° C., then transferred without contacting, and dried in a helical air cushion dryer with the dry air of a dry-bulb temperature between 23° C. and 45° C. and a wet-bulb temperature between 15° C. and 21° C.

After drying, the humidity was adjusted to 40% RH to 60% RH at 25° C., and the film surface was heated to a temperature between 70° C. and 90° C. After heating, the film surface was cooled to 25° C.

The mat degree of the formed thermal-developable photosensitive material was a Beck flatness of 550 seconds on the surface of the photosensitive layer, and 130 seconds on the back face. The pH measured on the film surface of the photosensitive layer surface side was 6.0.

<Preparation of Thermal-developable Photosensitive Material-2>

Thermal-developable photosensitive material-2 was prepared in the same manner as the thermal-developable photosensitive material-1, except that the emulsion layer coating liquid-1 was changed to the emulsion layer coating liquid-2, and the yellow dye compound 15 was excluded from the anti-halation layer.

The coating quantity (g/m$^2$) of each compound as the emulsion layer in this time is as follows:

| | |
|---|---|
| Silver behenate | 6.19 |
| Pigment (C. I. Pigment Blue 60) | 0.036 |
| Polyhalogen compound-2 | 0.13 |
| Polyhalogen compound-3 | 0.41 |
| Phthalazine compound-1 | 0.21 |
| SBR latex | 11.1 |
| Reducer complex-3 | 1.54 |
| Mercapto compound-1 | 0.002 |
| Silver halide (as Ag) | 0.10 |

<Preparation of Thermal-developable Photosensitive Material-3>

Thermal-developable photosensitive material-3 was prepared in the same manner as the thermal-developable photosensitive material-1, except that the emulsion layer coating liquid-1 was changed to the emulsion layer coating liquid-3; the yellow dye compound 15 was excluded from the antihalation layer; fluorine-based surfactants F-1, F-2, F-3, and F-4 in the second protecting layer and the back-face protecting layer were changed to fluorine-based surfactants F-5, F-6, F-7, and F-8 of the same masses, respectively.

The coating quantity ($g/m^2$) of each compound as the emulsion layer in this time is as follows:

| | |
|---|---|
| Silver behenate | 5.57 |
| Pigment (C. I. Pigment Blue 60) | 0.032 |
| Reducer-4 | 0.40 |
| Reducer-5 | 0.36 |
| Polyhalogen compound-2 | 0.12 |
| Polyhalogen compound-3 | 0.37 |
| Phthalazine compound-1 | 0.19 |
| SBR latex | 10.0 |
| Hydrogen-bondable compound-2 | 0.59 |
| Mercapto compound-1 | 0.002 |
| Silver halide (as Ag) | 0.09 |

(Evaluation of Photographic Performance)

With a Fuji Medical Dry Laser Imager FM-DPL (incorporating a 660-nm semiconductor laser of a maximum output of 60 mW (IIIB), a photographic material was exposed and heat-developed (total of 24 seconds by four panel heaters set to 112° C., 119° C., 121° C., and 121° C.), and the obtained image was evaluated with a photographic densitometer.

As described above, in the inspection method and apparatus of the present invention for inspecting a photosensitive material for surface defects, specular reflected light in the reflected part of inspection light reflected by the thermal-developable photosensitive material is cut out and diffuse reflected light in the reflected part of the inspection light is received, thereby enabling a defective surface portion across which only a small change in diffuse reflectance is recognized to be detected with efficiency.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A surface defect inspection method of inspecting a photosensitive material for defective surface portions by using a reflex-type optical sensor, comprising the steps of:

irradiating the photosensitive material with inspection light from a light-emitting portion of the reflex-type optical sensor;

receiving, through a light-receiving portion of the reflex-type optical sensor, light in a reflected part of the inspection light reflected by the photosensitive material while cutting out specular reflected light in the reflected part of the inspection light; and checking a defective surface portion in the photosensitive material in accordance with a change in a quantity of the light received through the light-receiving portion.

2. The surface defect inspection method according to claim 1, wherein a selection is enabled from a state where the specular reflected light is cut out and a state where the specular reflected light is not cut out.

3. The surface defect inspection method according to claim 1, wherein the photosensitive material is a thermal-developable photosensitive material.

4. The surface defect inspection method according to claim 3, wherein a selection is enabled from a state where the specular reflected light is cut out and a state where the specular reflected light is not cut out.

5. The surface defect inspection method according to claim 1, wherein the defective surface portion is checked by using a transmission-type optical sensor for inspection using light transmitted through the photosensitive material as well as the reflex-type optical sensor.

6. The surface defect inspection method according to claim 5, wherein a selection is enabled from a state where the specular reflected light is cut out and a state where the specular reflected light is not cut out.

7. The surface defect inspection method according to claim 5, wherein the photosensitive material is a thermal-developable photosensitive material.

8. The surface defect inspection method according to claim 7, wherein a selection is enabled from a state where the specular reflected light is cut out and a state where the specular reflected light is not cut out.

9. A surface defect inspection apparatus which inspects a photosensitive material for defective surface portions by using a reflex-type optical sensor, wherein the reflex-type optical sensor comprises:

a light-emitting portion which irradiates the photosensitive material with inspection light;

a light-receiving portion which receives light in a reflected part of the inspection light reflected by the photosensitive material; and a shielding member which cuts out specular reflected light in the reflected part of the inspection light traveling to the light-receiving portion.

* * * * *